US012214260B2

United States Patent
Intonato et al.

(10) Patent No.: US 12,214,260 B2
(45) Date of Patent: Feb. 4, 2025

(54) EXERCISE MACHINE CONTROLS

(71) Applicant: Peloton Interactive, Inc., New York, NY (US)

(72) Inventors: Joseph Intonato, Brooklyn, NY (US); Betina Evancha, Brooklyn, NY (US)

(73) Assignee: Peloton Interactive, Inc., New York, NY (US)

( * ) Notice: Subject to any disclaimer, the term of this patent is extended or adjusted under 35 U.S.C. 154(b) by 256 days.

(21) Appl. No.: 17/862,139

(22) Filed: Jul. 11, 2022

(65) Prior Publication Data

US 2022/0339504 A1 Oct. 27, 2022

Related U.S. Application Data

(63) Continuation of application No. 16/510,619, filed on Jul. 12, 2019, now Pat. No. 11,383,134, which is a (Continued)

(51) Int. Cl.
*A63B 24/00* (2006.01)
*A63B 22/02* (2006.01)
*A63B 71/06* (2006.01)

(52) U.S. Cl.
CPC ........ *A63B 24/0087* (2013.01); *A63B 22/025* (2015.10); *A63B 24/0075* (2013.01); (Continued)

(58) Field of Classification Search
CPC .............. A63B 24/0087; A63B 22/025; A63B 24/0075; A63B 71/0622; (Continued)

(56) References Cited

U.S. PATENT DOCUMENTS 32,345 A * 5/1861 Bartholow ................ F42B 5/18 102/431
219,059 A * 9/1879 Anders .................. G10K 1/063 379/418

(Continued)

FOREIGN PATENT DOCUMENTS

CN 2877780 3/2007
CN 101108273 A 1/2008

(Continued)

OTHER PUBLICATIONS

"CompuTrainer", Racermate, 2017, retrieved Nov. 30, 2018 from <<http://www/racermateinc.com/computrainer/>>, 1 page.

(Continued)

*Primary Examiner* — Garrett K Atkinson
(74) *Attorney, Agent, or Firm* — Haynes and Boone, LLP

(57) ABSTRACT

A method includes providing a first video file to a plurality of exercise machines, the first video file including content associated with an exercise class. The method also includes receiving user data from the plurality of exercise machines, the user data including respective settings associated with a common performance metric. In such a method, the respective settings are used on the plurality of exercise machines during playback of a particular part of the first video file. The method also includes identifying a timestamp associated with the particular part of the first video file, and generating an executable control corresponding to the performance metric. The method further includes generating a second video file comprising the content and the executable control. In such methods, playback of the second video file causes display of the executable control at a part of the second video file corresponding to the timestamp.

20 Claims, 14 Drawing Sheets

Related U.S. Application Data continuation-in-part of application No. 16/217,548, filed on Dec. 12, 2018, now Pat. No. 11,298,591, which is a continuation-in-part of application No. 15/863,057, filed on Jan. 5, 2018, now Pat. No. 11,311,791, which is a continuation-in-part of application No. 15/686,875, filed on Aug. 25, 2017, now Pat. No. 10,864,406, application No. 17/862,139 is a continuation-in-part of application No. 17/346,166, filed on Jun. 11, 2021, which is a continuation of application No. PCT/US2019/065882, filed on Dec. 12, 2019, which is a continuation of application No. 16/217,548, filed on Dec. 12, 2018, now Pat. No. 11,298,591, which is a continuation-in-part of application No. 15/863,057, filed on Jan. 5, 2018, now Pat. No. 11,311,791, which is a continuation-in-part of application No. 15/686,875, filed on Aug. 25, 2017, now Pat. No. 10,864,406, said application No. 17/346,166 is a continuation of application No. 16/217,548, filed on Dec. 12, 2018, now Pat. No. 11,298,591, which is a continuation-in-part of application No. 15/863,057, filed on Jan. 5, 2018, now Pat. No. 11,311,791, which is a continuation-in-part of application No. 15/686,875, filed on Aug. 25, 2017, now Pat. No. 10,864,406, application No. 17/862,139 is a continuation-in-part of application No. 17/572,576, filed on Jan. 10, 2022, which is a continuation of application No. 15/863,596, filed on Jan. 5, 2018, now Pat. No. 11,219,799, which is a continuation-in-part of application No. 15/686,875, filed on Aug. 25, 2017, now Pat. No. 10,864,406.

(60) Provisional application No. 62/380,412, filed on Aug. 27, 2016.

(52) U.S. Cl.
CPC .. *A63B 71/0622* (2013.01); *A63B 2024/0078* (2013.01); *A63B 2024/009* (2013.01); *A63B 2024/0093* (2013.01); *A63B 2071/063* (2013.01); *A63B 2071/0658* (2013.01); *A63B 2209/00* (2013.01); *A63B 2225/093* (2013.01)

(58) Field of Classification Search
CPC ...... A63B 2024/0078; A63B 2024/009; A63B 2024/0093; A63B 2071/063; A63B 2071/0658; A63B 2209/00; A63B 2225/093; A63B 71/0669; A63B 2024/0068; A63B 2024/0081; A63B 2071/0625; A63B 2071/0641; A63B 2071/0691; A63B 2220/18; A63B 2220/30; A63B 2220/40; A63B 2220/62; A63B 2220/806; A63B 2220/833; A63B 2225/105; A63B 2225/50; A63B 2230/06; A63B 2230/40; A63B 2230/75; A63B 24/0062; A63B 22/0605; A63B 22/0664; A63B 24/0084; A63B 71/0616; A63B 71/0619; A63B 71/0686; A63B 2071/065; A63B 2071/0683; A63B 2071/0694; A63B 2220/17; A63B 2220/20; A63B 2220/34; A63B 2220/50; A63B 2220/80; A63B 2220/808; A63B 2220/836; A63B 2225/20; A63B 2230/01; A63B 2230/30; A63B 2230/50; A63B 22/02; G16H 20/30; G16H 40/63; G16H 40/67
See application file for complete search history.

(56) References Cited

U.S. PATENT DOCUMENTS 3,976,192 A 8/1976 Muller
4,591,147 A 5/1986 Smith et al.
4,614,337 A 9/1986 Schonenberger
4,771,148 A 9/1988 Bersonnet
D303,414 S 9/1989 Armstrong et al.
5,029,801 A 7/1991 Dalebout et al.
5,104,120 A * 4/1992 Watterson ............ A63B 22/025 482/7
D330,399 S 10/1992 Furline
5,178,594 A 1/1993 Wu
5,336,145 A 8/1994 Keiser
5,383,826 A 1/1995 Michael
5,441,468 A 8/1995 Deckers et al.
5,458,548 A 10/1995 Crossing et al.
5,547,439 A 8/1996 Rawls et al.
5,656,000 A 8/1997 Russell
5,947,868 A * 9/1999 Dugan .................. A63F 13/211 482/4
5,984,838 A 11/1999 Wang et al.
5,989,161 A 11/1999 Wang et al.
6,042,514 A 3/2000 Abelbeck
6,050,924 A 4/2000 Shea
6,171,218 B1 1/2001 Shea
6,231,482 B1 5/2001 Thompson
6,409,633 B1 6/2002 Abelbeck
6,438,241 B1 8/2002 Silfvast et al.
6,471,622 B1 10/2002 Hammer et al.
6,601,016 B1 7/2003 Brown et al.
6,626,803 B1 9/2003 Oglesby et al.
6,648,798 B2 11/2003 Yoo
6,695,751 B1 2/2004 Hsu
6,702,719 B1 3/2004 Brown et al.
6,749,536 B1 6/2004 Cuskaden et al.
6,764,430 B1 7/2004 Fencel
6,830,541 B2 12/2004 Wu
6,899,659 B2 5/2005 Anderson et al.
6,902,513 B1 * 6/2005 McClure ............ A63B 24/0006 482/4
6,923,746 B1 8/2005 Skowronski et al.
6,984,193 B2 1/2006 Chen
6,997,853 B1 2/2006 Cuskaden et al.
7,153,241 B2 12/2006 Wang
7,252,624 B2 8/2007 Wu et al.
7,455,620 B2 11/2008 Frykman et al.
7,562,761 B2 7/2009 Tasma et al.
7,594,878 B1 9/2009 Joannou
7,618,352 B1 11/2009 Wei
D606,599 S 12/2009 Murray et al.
7,628,730 B1 12/2009 Watterson et al.
7,746,997 B2 * 6/2010 Brunson .................. G09B 5/06 434/323
7,927,253 B2 * 4/2011 Vincent ................ A63F 13/211 482/8
8,001,472 B2 * 8/2011 Gilley .................... A63B 22/02 715/834
8,012,067 B2 9/2011 Joannou
8,348,813 B2 1/2013 Huang
8,376,910 B2 * 2/2013 Cheung .................. G06F 3/011 482/901
8,545,369 B2 * 10/2013 Cheung .............. A63B 24/0084 482/8
8,579,767 B2 * 11/2013 Ellis ...................... G16H 20/10 482/901
8,608,624 B2 12/2013 Shabodyash et al.
8,829,376 B2 9/2014 Wei
8,986,169 B2 3/2015 Bayerlein et al.
9,174,085 B2 * 11/2015 Foley ...................... G16Z 99/00
9,254,411 B1 2/2016 Chang
9,452,314 B2 9/2016 Hou
9,452,315 B1 9/2016 Murray et al.
9,463,349 B1 10/2016 Chang
9,579,544 B2 2/2017 Watterson
9,616,278 B2 4/2017 Olson
9,623,285 B1 * 4/2017 Ruiz ....................... G01C 9/00

(56) References Cited

U.S. PATENT DOCUMENTS 9,636,567 B2 * 5/2017 Brammer ........... A63B 71/0622
9,649,528 B2 5/2017 Hou
9,675,839 B2 6/2017 Dalebout et al.
9,682,307 B2 6/2017 Dalebout
9,694,234 B2 7/2017 Dalebout et al.
9,694,242 B2 7/2017 Ashby et al.
9,713,742 B2 7/2017 Pasini et al.
9,767,785 B2 9/2017 Ashby et al.
9,782,625 B1 10/2017 Blum et al.
9,808,672 B2 11/2017 Dalebout
9,814,929 B2 11/2017 Moser
9,814,930 B2 11/2017 Manzke et al.
10,009,644 B2 * 6/2018 Aimone ............... A61B 5/0022
10,010,748 B1 7/2018 Weinstein et al.
10,617,331 B1 * 4/2020 Solberg .............. A63B 24/0087
2002/0091627 A9 7/2002 Yang
2003/0093248 A1 * 5/2003 Vock .................... A42B 3/0433 702/188
2003/0199366 A1 * 10/2003 Anderson .......... A63B 22/0242 482/54
2003/0216225 A1 11/2003 Pan
2004/0102931 A1 * 5/2004 Ellis ..................... A61B 5/0833 702/188
2004/0121884 A1 6/2004 Chang
2004/0166995 A1 8/2004 Wu
2005/0054490 A1 3/2005 Chou
2005/0137062 A1 6/2005 Kuokkanen
2005/0239601 A1 10/2005 Thomas
2006/0009332 A1 1/2006 Jones
2006/0058160 A1 3/2006 Lee et al.
2006/0122035 A1 * 6/2006 Felix .................. A63B 71/0622 482/8
2006/0136173 A1 * 6/2006 Case .................... G01C 22/006 702/182
2006/0189439 A1 8/2006 Baudhuin
2006/0207867 A1 9/2006 Waddington
2007/0032345 A1 * 2/2007 Padmanabhan ........ A63B 24/00 482/8
2007/0049466 A1 * 3/2007 Hubbard ................ A63B 24/00 482/8
2007/0072743 A1 3/2007 Severin et al.
2007/0105693 A1 5/2007 Wang
2007/0116207 A1 * 5/2007 Brunson .................. G09B 7/02 379/90.01
2007/0219059 A1 * 9/2007 Schwartz ............... A61B 5/329 482/8
2007/0281831 A1 12/2007 Wang
2008/0015089 A1 * 1/2008 Hurwitz .................... B60T 7/12 482/8
2008/0076637 A1 * 3/2008 Gilley ................ G06Q 30/0201 482/9
2008/0086318 A1 * 4/2008 Gilley .................... G16H 10/20 705/319
2008/0116036 A1 5/2008 Tasma et al.
2008/0242511 A1 10/2008 Munoz et al.
2009/0011907 A1 1/2009 Radow et al.
2009/0098524 A1 * 4/2009 Walton ..................... G09B 5/14 434/350
2009/0233771 A1 * 9/2009 Quatrochi .......... A63B 71/0622 434/247
2009/0291805 A1 * 11/2009 Blum ....................... A63B 6/00 482/9
2010/0048358 A1 * 2/2010 Tchao ................ A63B 24/0084 482/8
2010/0062904 A1 3/2010 Crawford et al.
2010/0160115 A1 6/2010 Morris et al.
2011/0082008 A1 * 4/2011 Cheung ............. A63B 24/0062 482/8
2011/0190097 A1 8/2011 Daly et al.
2011/0306911 A1 12/2011 Tran
2012/0088633 A1 4/2012 Crafton
2012/0179772 A1 7/2012 Hinnebusch
2012/0237911 A1 9/2012 Watterson
2013/0125025 A1 * 5/2013 Cheung ................... G06F 3/048 715/753
2013/0137073 A1 5/2013 Nacey et al.
2013/0178337 A1 7/2013 Brammer
2013/0237374 A1 * 9/2013 Ashby ................ A63B 71/0054 482/4
2013/0267386 A1 10/2013 Her
2013/0281241 A1 10/2013 Watterson et al.
2013/0346168 A1 12/2013 Zhou et al.
2014/0038781 A1 2/2014 Foley
2014/0082526 A1 3/2014 Park
2014/0172135 A1 * 6/2014 Eisner ..................... G06F 17/40 700/91
2014/0223462 A1 * 8/2014 Aimone ................. A61B 5/369 725/10
2015/0181314 A1 * 6/2015 Swanson ................. G01S 19/19 340/870.07
2015/0182800 A1 * 7/2015 Watterson .............. A63B 22/02 482/4
2015/0182845 A1 7/2015 Kolman et al.
2015/0190671 A1 7/2015 Golen, Jr.
2015/0224364 A1 8/2015 Hsieh
2015/0238817 A1 8/2015 Watterson
2015/0238819 A1 8/2015 Volkerink et al.
2015/0240507 A1 * 8/2015 Kolodny ................... E04H 3/14 52/234
2015/0273272 A1 10/2015 Wang
2016/0023044 A1 1/2016 Dalebout
2016/0023045 A1 1/2016 Dalebout
2016/0023049 A1 1/2016 Dalebout
2016/0103970 A1 4/2016 Lie et al.
2016/0129311 A1 5/2016 Yang
2016/0166877 A1 6/2016 Cei et al.
2016/0170436 A1 6/2016 Farrar et al.
2016/0181028 A1 6/2016 Ebrom et al.
2016/0199695 A1 7/2016 Armstrong
2016/0287930 A1 10/2016 Moser
2017/0103440 A1 4/2017 Xing et al.
2017/0128769 A1 * 5/2017 Long ....................... H04L 67/10
2017/0186444 A1 * 6/2017 Lu .......................... G10L 15/08
2017/0281079 A1 * 10/2017 Nachman ............. H04L 67/306
2017/0326411 A1 11/2017 Watterson
2017/0333751 A1 11/2017 Seol
2017/0340917 A1 11/2017 Chang
2018/0036593 A1 2/2018 Ridgel et al.
2018/0056132 A1 * 3/2018 Foley ................. A63B 23/0405
2018/0104564 A1 * 4/2018 Cardon ............. A63B 71/0622
2018/0126248 A1 * 5/2018 Dion ........................ A63B 1/00
2018/0126249 A1 * 5/2018 Consiglio .......... A63B 22/0023
2018/0140903 A1 * 5/2018 Poure ................ A63B 23/1227
2018/0225367 A1 * 8/2018 Glen ....................... G06F 16/38
2018/0308389 A1 10/2018 Moser et al.
2019/0111318 A1 4/2019 Evancha et al.
2019/0143194 A1 5/2019 Evancha et al.
2020/0014967 A1 * 1/2020 Putnam ..................... G06F 3/16
2020/0015736 A1 * 1/2020 Alhathal .................. A61B 5/11
2020/0332990 A1 * 10/2020 Bayerlein ............. A63B 22/02
2021/0093921 A1 4/2021 Foley et al.

FOREIGN PATENT DOCUMENTS

CN 101454050 A 6/2009
CN 101766891 7/2010
CN 104056442 A 9/2014
CN 105409145 A 3/2016
CN 205595259 U 9/2016
CN 106470739 A 3/2017
CN 206544889 U 10/2017
CN 108853946 A 11/2018
CN 2020106686316 8/2022
CN 201980091994.3 9/2022
CN 202210704768.1 11/2023
EP 0919259 6/1999
EP 2964349 1/2016
EP 19895217.8 8/2022
JP 2004-331004 A 11/2004
JP 2012-050584 A 3/2012
JP 2016510234 A 4/2016

(56) References Cited

FOREIGN PATENT DOCUMENTS

| | | | |
|---|---|---|---|
| JP | 2016163684 | A | 9/2016 |
| JP | 2017199318 | A | 11/2017 |
| JP | 2018-175670 | A | 11/2018 |
| JP | 2021-533174 | | 3/2023 |
| JP | 2020-119118 | | 8/2023 |
| TW | 201703500 | A | 1/2017 |
| TW | I606856 | B | 12/2017 |
| TW | 201802767 | A | 1/2018 |
| TW | I644706 | | 12/2018 |
| TW | 109123381 | | 8/2023 |
| WO | WO 1997/041925 | | 11/1997 |
| WO | WO 2005/087323 | | 9/2005 |
| WO | WO 2017/209500 | | 12/2017 |
| WO | WO 2019/143488 | | 7/2019 |

OTHER PUBLICATIONS

"Netathlon", WebRacing, 2014, retrieved Nov. 30, 2018 from <<http://webracinginc.com/products_netathlon.htm>>, 3 pages.

* cited by examiner

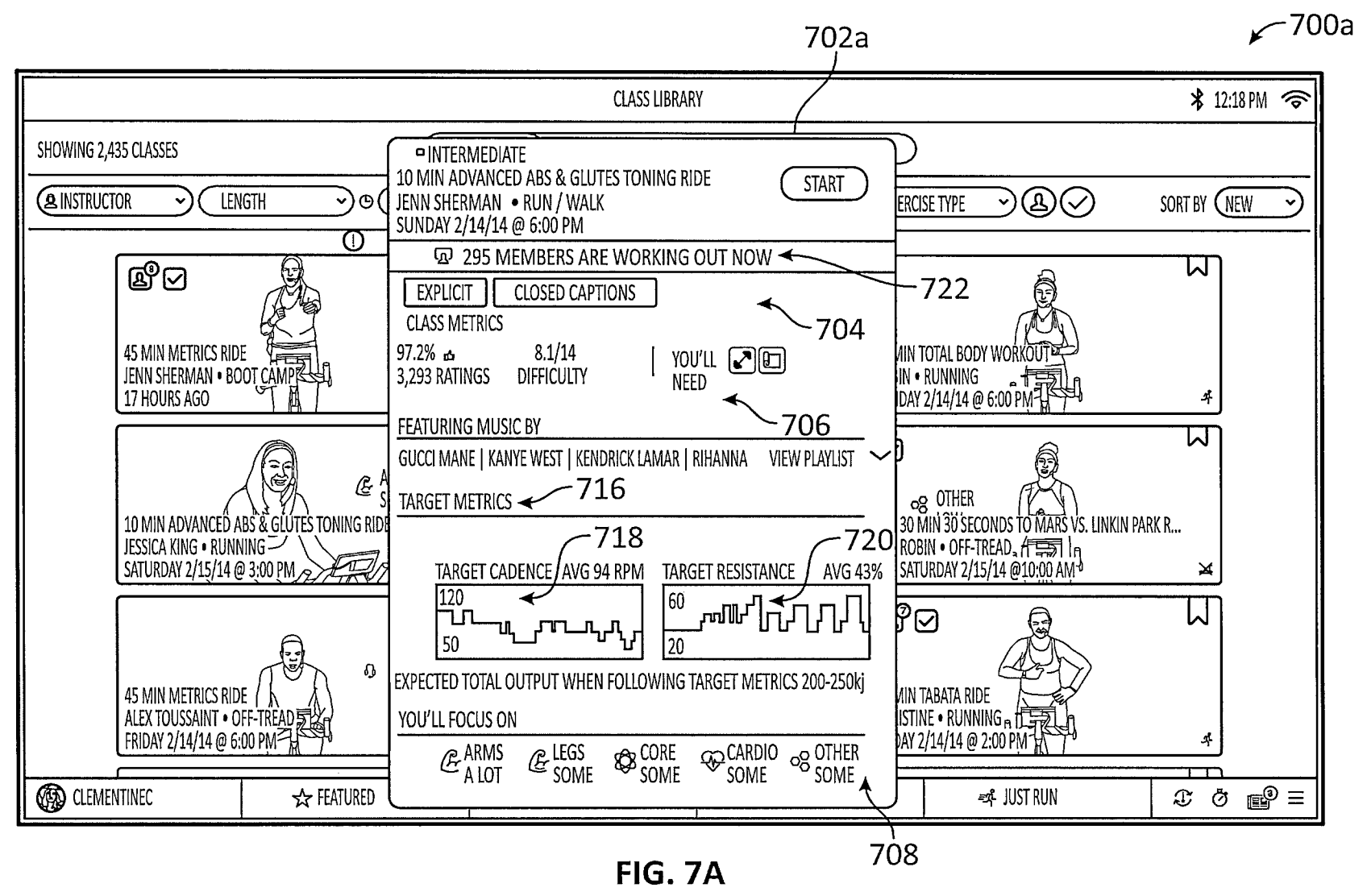

CLASS LIBRARY

SHOWING 2,435 CLASSES

INSTRUCTOR

LENGTH

ERCISE TYPE

SORT BY NEW

12:18 PM

INTERMEDIATE

10 MIN ADVANCED ABS & GLUTES TONING RIDE

JENN SHERMAN • RUN / WALK

SUNDAY 2/14/14 @ 6:00 PM

START

295 MEMBERS ARE WORKING OUT NOW

722

EXPLICIT

CLOSED CAPTIONS

CLASS METRICS

704

97.2%

3,293 RATINGS 8.1/14

DIFFICULTY

YOU'LL NEED

706

FEATURING MUSIC BY

GUCCI MANE | KANYE WEST | KENDRICK LAMAR | RIHANNA

VIEW PLAYLIST

TARGET METRICS

716

718

720

TARGET CADENCE AVG 94 RPM

120

50

TARGET RESISTANCE AVG 43%

60

20

EXPECTED TOTAL OUTPUT WHEN FOLLOWING TARGET METRICS 200-250kj

YOU'LL FOCUS ON

ARMS A LOT

LEGS SOME

CORE SOME

CARDIO SOME

OTHER SOME

708

45 MIN METRICS RIDE

JENN SHERMAN • BOOT CAMP

17 HOURS AGO

10 MIN ADVANCED ABS & GLUTES TONING RIDE

JESSICA KING • RUNNING

SATURDAY 2/15/14 @ 3:00 PM

45 MIN METRICS RIDE

ALEX TOUSSAINT • OFF-TREAD

FRIDAY 2/14/14 @ 6:00 PM

MIN TOTAL BODY WORKOUT

IN • RUNNING

DAY 2/14/14 @ 6:00 PM

OTHER

30 MIN 30 SECONDS TO MARS VS. LINKIN PARK R...

ROBIN • OFF-TREAD

SATURDAY 2/15/14 @10:00 AM

MIN TABATA RIDE

ISTINE • RUNNING

DAY 2/14/14 @ 2:00 PM

CLEMENTINEC

FEATURED

JUST RUN

FIG. 7A

EXERCISE MACHINE CONTROLS

CROSS-REFERENCE TO RELATED APPLICATIONS

The present application is a continuation of U.S. patent application Ser. No. 16/510,619 filed Jul. 12, 2019, which is a continuation-in-part of U.S. patent application Ser. No. 16/217,548 filed Dec. 12, 2018, which is a continuation-in-part of U.S. patent application Ser. No. 15/863,057 filed Jan. 5, 2018, which is a continuation-in-part of U.S. patent application Ser. No. 15/686,875 filed Aug. 25, 2017, which claims the benefit of U.S. Provisional Patent Application No. 62/380,412 filed Aug. 27, 2016, the entire disclosures of which are incorporated herein by reference.

The present application is a continuation-in part of U.S. patent application Ser. No. 17/346,166 filed Jun. 11, 2021, which is a continuation of International Patent Application No. PCT/US2019/065882 filed Dec. 12, 2019, which is a continuation of U.S. patent application Ser. No. 16/217,548 filed Dec. 12, 2018, which is a continuation-in-part of U.S. patent application Ser. No. 15/863,057 filed Jan. 5, 2018, which is a continuation-in-part of U.S. patent application Ser. No. 15/686,875 filed Aug. 25, 2017, which claims the benefit of U.S. Provisional Patent Application No. 62/380,412 filed Aug. 27, 2016, the entire disclosures of which are incorporated herein by reference.

U.S. patent application Ser. No. 17/346,166 is a continuation of U.S. patent application Ser. No. 16/217,548 filed Dec. 12, 2018, which is a continuation-in-part of U.S. patent application Ser. No. 15/863,057 filed Jan. 5, 2018, which is a continuation-in-part of U.S. patent application Ser. No. 15/686,875 filed Aug. 25, 2017, which claims the benefit of U.S. Provisional Patent Application No. 62/380,412 filed Aug. 27, 2016, the entire disclosures of which are incorporated herein by reference.

The present application is a continuation-in part of U.S. patent application Ser. No. 17/572,576 filed Jan. 10, 2022, which is a continuation of U.S. patent application Ser. No. 15/863,596 filed Jan. 5, 2018, which is a continuation-in-part of U.S. patent application Ser. No. 15/686,875 filed Aug. 25, 2017, which claims the benefit of U.S. Provisional Patent Application No. 62/380,412 filed Aug. 27, 2016, the entire disclosures of which are incorporated herein by reference.

FIELD OF THE INVENTION

This application relates generally to the field of exercise equipment and methods associated therewith. In particular, this application relates to executable controls and control methods associated with exercise machines.

BACKGROUND

Exercise has become an increasingly important aspect of daily life, and most exercise regimens commonly involve the use of elliptical machines, stationary bicycles, rowing machines, treadmills, or other exercise machines. Such exercise machines are typically designed for use in a gym or other exercise facility, and may be configured such that a user can participate in various exercise classes, training programs, or other activities using such machines. In particular, such exercise machines generally provide the user with one or more buttons, switches, knobs, levers, or other mechanisms that enable the user to control various parameters of the exercise machine during use. For instance, a treadmill may include one or more controls dedicated to increasing and decreasing an incline of the treadmill deck, increasing and decreasing a speed of the treadmill belt, or modifying other parameters of the treadmill as the user walks, jogs, sprints, or performs various other activities on the treadmill. Similarly, a stationary bicycle may include one or more controls dedicated to increasing and decreasing a braking resistance of a flywheel of the bicycle, increasing and decreasing a pedal speed or cadence of the bicycle, or modifying other parameters of the stationary bicycle during use.

While such controls are commonplace on treadmills, stationary bicycles, elliptical machines, and other known exercise machines, such controls can be challenging to use in some situations. For example, due to the dynamic nature of the motion-based activities typically performed on such exercise machines (e.g., running, cycling, etc.), it can be difficult for a user to manipulate such controls during a workout. Moreover, even if a user is able to manipulate such controls while running, cycling, or performing other motion-based activities, such controls may not be optimized for enabling the user to select a particular setting or other parameter of the exercise machine, with accuracy, as such motion-based activities are being performed. Additionally, such controls typically do not correspond to verbal cues, suggestions, directions, comments, or other performance commands uttered by an instructor during an exercise class being performed using the exercise machine.

Example embodiments of the present disclosure are directed toward addressing one or more of the deficiencies of known exercise machines noted above.

SUMMARY OF THE INVENTION

In an example embodiment of the present disclosure, a method includes capturing audio content and video content of an instructor performing an exercise class, identifying a performance command included in the audio content, the performance command being uttered by the instructor during the exercise class, and identifying a timestamp associated with the performance command. Such an example method also includes generating an executable control corresponding to the performance command, and generating a video file comprising the audio content, the video content, and the executable control. In such examples, playback of the video file causes display of the executable control at a part of the video file corresponding to the timestamp. Such a method also includes providing the video file to an exercise machine, via a network, based at least in part on a request received via the network.

In another example embodiment, a method includes providing a first video file to a plurality of exercise machines, the first video file including content associated with an exercise class. The method also includes receiving user data from the plurality of exercise machines, the user data including respective settings associated with a common performance metric, the respective settings being used on the plurality of exercise machines during playback of a particular part of the first video file. Such an example method further includes identifying a timestamp associated with the particular part of the first video file, and generating an executable control corresponding to the performance metric. The method also includes generating a second video file comprising the content and the executable control. In such an example method, playback of the second video file causes display of the executable control at a part of the second video file corresponding to the timestamp.

In yet another example embodiment, a method includes receiving a video file at an exercise machine via a network, the video file including content associated with an exercise class, and providing the content via a display associated with the exercise machine, wherein providing the content includes displaying an executable control included in the video file, via the display, during a particular part of the video file. Such an example method also includes receiving user data collected while the executable control is displayed, the user data including a first setting of the exercise machine selected by a user during the particular part of the video file. Such a method further includes determining a difference between the first setting and a second setting of the executable control, generating an accuracy metric based at least in part on the difference, and providing the accuracy metric via the display.

BRIEF DESCRIPTION OF THE DRAWINGS

The detailed description is described with reference to the accompanying figures. In the figures, the left-most digit of a reference number identifies the figure in which the reference number first appears. The same reference numbers in different figures indicate similar or identical items.

FIG. 7 illustrates yet another example user interface of the present disclosure showing information corresponding to an exercise class.

FIG. 7A illustrates still another example user interface of the present disclosure showing information corresponding to an exercise class.

DETAILED DESCRIPTION

Figure 1:
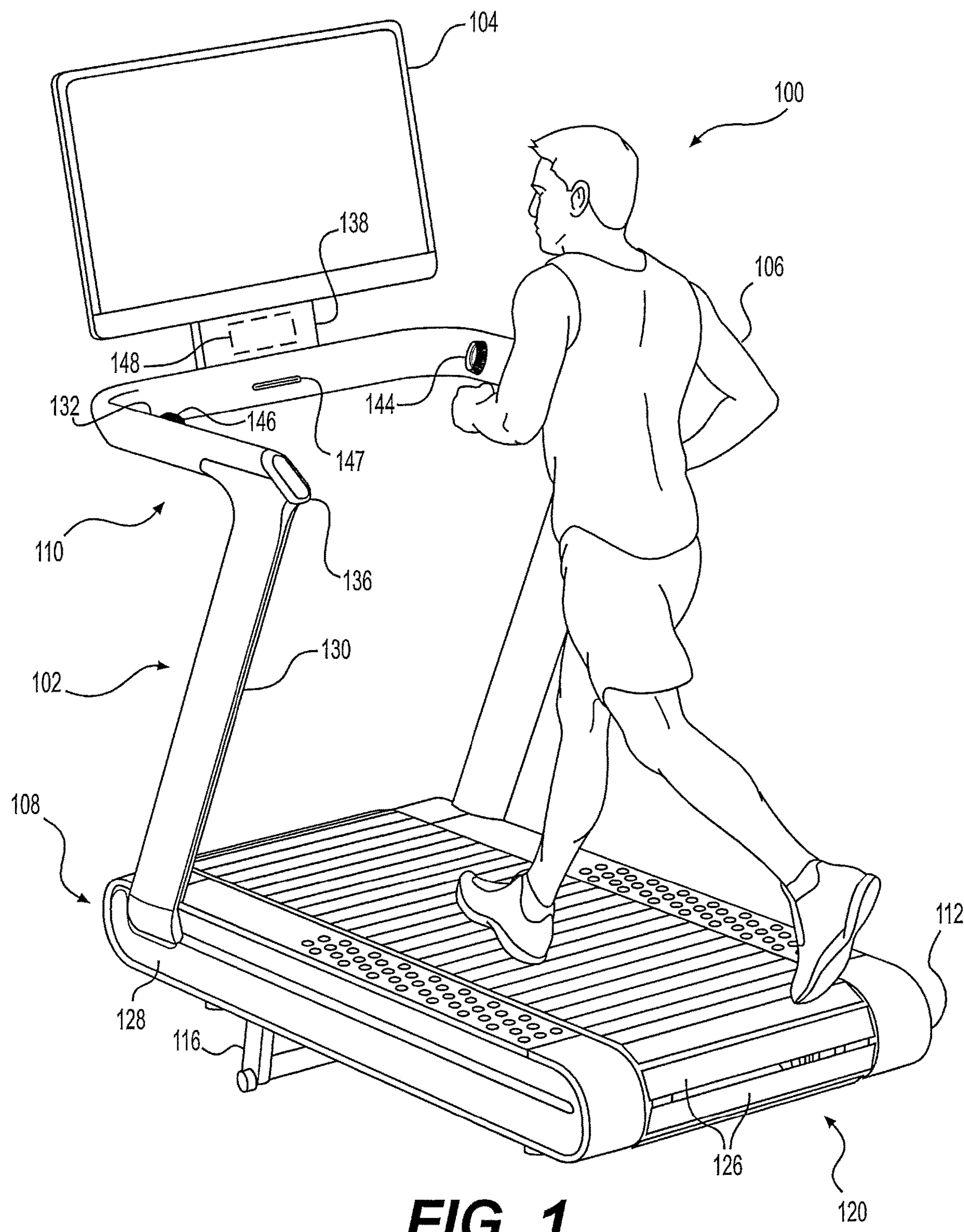
FIG. 1 is a perspective view of an example exercise machine as disclosed herein with a user shown.

The following description is presented to enable any person skilled in the art to make and use aspects of the example embodiments described herein. For purposes of explanation, specific nomenclature is set forth to provide a thorough understanding of the present invention. Descriptions of specific embodiments or applications are provided only as examples. Various modifications to the embodiments will be readily apparent to those skilled in the art, and general principles defined herein may be applied to other embodiments and applications without departing from the spirit and scope of the present disclosure. Thus, the present disclosure is not intended to be limited to the embodiments shown, but is to be accorded the widest possible scope consistent with the principles and features disclosed herein.

Example embodiments of the present disclosure include exercise machines, networked exercise systems, and corresponding methods whereby one or more exercise devices, such as treadmills, rowing machines, stationary bicycles, elliptical trainers, or any other suitable equipment may be equipped with an associated local system that allows a user to fully participate in live or recorded exercise classes from any location that can access a suitable communications network. The example exercise machines of the present disclosure include one or more displays configured to provide various controls operable to change parameters of the exercise machines. In particular, the displays of the present disclosure may be configured to provide user interfaces that include one or more executable controls operable to modify respective parameters of the exercise machine while the user of the machine is participating in an exercise class and/or otherwise using the exercise machine. In some examples, such executable controls may correspond to verbal cues, suggestions, directions, comments, or other performance commands uttered by an instructor during an exercise class. In some examples, such executable controls may include a setting corresponding to a relatively specific instruction or command given by the instructor. In other examples, on the other hand, such executable controls may include a setting corresponding to a relatively vague or abstract command given by the instructor during the exercise class. Additionally or alternatively, such executable controls may correspond to user data received from a plurality of exercise machines, wherein the user data includes respective settings used on the plurality of exercise machines during playback of an exercise class.

Thus, the exercise machines, executable controls, and corresponding methods described herein, may enable a user to easily and accurately modify one or more parameters of an exercise machine while participating in an exercise class, and according to a control setting that is unique to the particular exercise class in which the user is participating. Various aspects of such exercise machines and executable controls will now be described in more detail.

Figure 2:
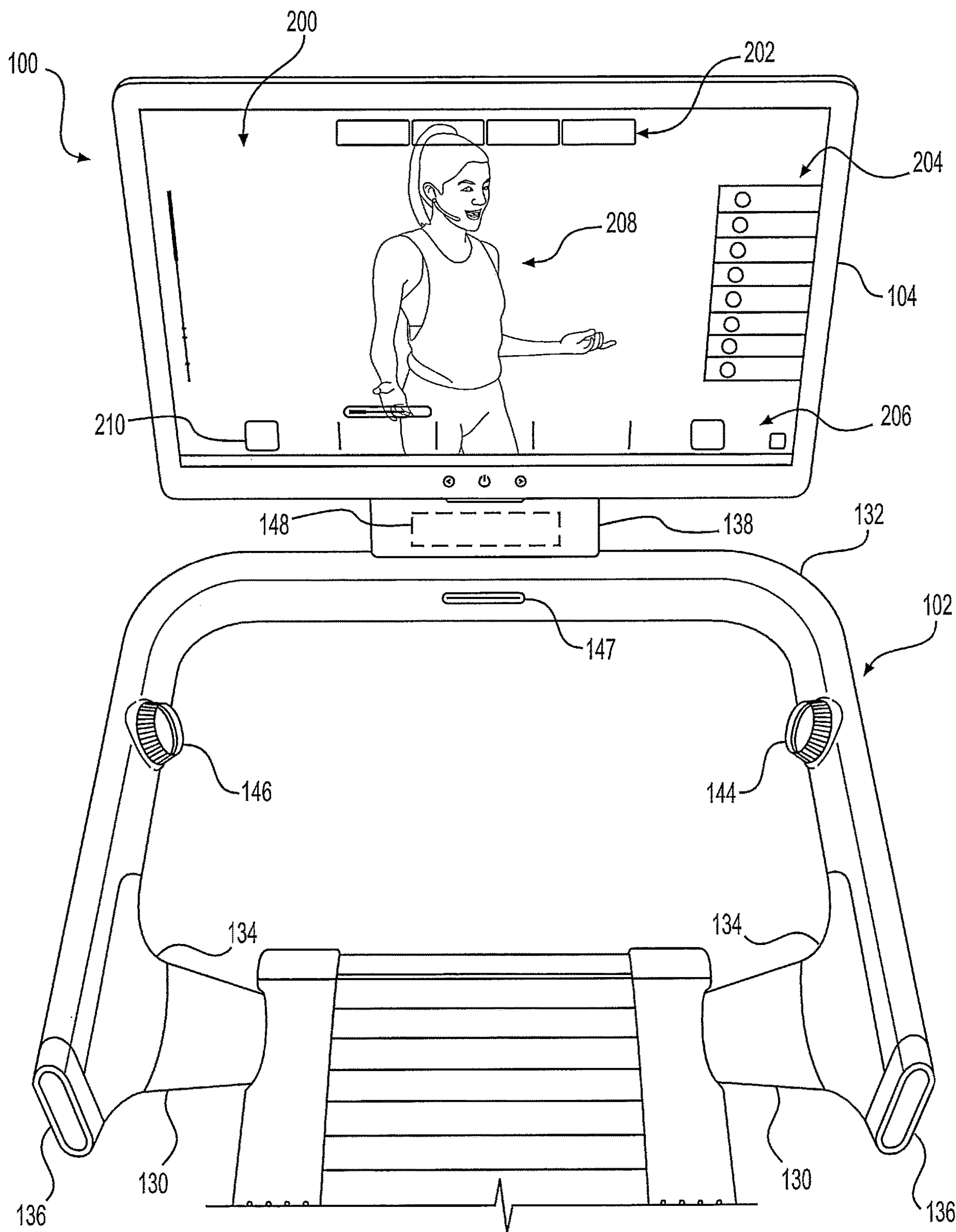
FIG. 2 illustrates another view of the example exercise machine shown in FIG. 1 including first and second rotary controls, and a display.

Referring generally to FIGS. 1 and 2, in various example embodiments of the present disclosure, a local system 100 may include an exercise machine 102, such as a treadmill, with integrated or connected digital hardware including one or more displays 104 for use in connection with an instructor-led exercise class and/or for displaying other digital content. While the exercise machine 102 may be described and/or otherwise referred to herein as a "treadmill 102," as noted above, example exercise machines 102 of the present disclosure may be any suitable type of exercise machine, including a rowing machine, stationary bicycle, elliptical trainer, stair climber, etc. Accordingly, any of the examples described herein may be applicable to, incorporated in, performed by, and/or otherwise associated with a treadmill, rowing machine, stationary bicycle, elliptical trainer, stair climber, etc. For ease of description, however, an exercise machine 102 comprising a treadmill will be referred to below unless otherwise specified.

In various example embodiments, the one or more displays 104 may be mounted directly to the exercise machine 102 or otherwise placed within view of a user 106. In various exemplary embodiments, the one or more displays 104 allow the user 106 to view content relating to a selected exercise class both while working out on the exercise machine 102 and while working out in one or more locations near or adjacent to the exercise machine 102. In some examples, the exercise machine 102 may also include a hinge, joint, pivot, bracket 138 or other suitable mechanism to allow for adjustment of the position or orientation of the display 104 relative to the user 106 whether the user 106 is working out on the exercise machine 102, or working out near or adjacent to the exercise machine 102.

In example embodiments in which the exercise machine 102 comprises a treadmill, the exercise machine 102 may generally include a lower assembly 108 and an upper assembly 110. The lower assembly 108 may generally include a deck 112 of the exercise machine 102 that provides support for the user 106 while the user 106 is working out on the exercise machine 102, as well as other components of both the lower assembly 108 and the upper assembly 110. For example, the deck 112 may support a first motor (not shown) of the exercise machine 102 configured to increase, decrease, and/or otherwise change an incline of the deck 112 relative to a support surface on which the exercise machine 102 is disposed. The deck 112 may also include one or more linkages 116 coupled to such a motor and configured to, for example, raise and lower the deck 112 by acting on the support surface when the motor is activated. The deck 112 may also include a second motor (not shown) configured to increase, decrease, and/or otherwise change a rotational speed of a belt 120 connected to the deck 112. The belt 120 may be rotatable relative to the deck 112 and, in particular, may be configured to revolve or otherwise move completely around (i.e., encircle) the deck 112 during use of the exercise machine 120. For example, in embodiments in which the exercise machine 102 comprises a treadmill, the belt 120 may support the user 106 and may repeatedly encircle the deck 112 as the user 106 runs, walks, and/or otherwise works out on the treadmill. Such an example belt 120 may include one or more continuous tracks (not shown) movably coupled to a gear, flywheel, pulley, and/or other component of the deck 112. In such examples, such a gear, flywheel, pulley, and/or other component of the deck112 may be coupled to an output shaft or other component of the second motor described above. In such examples, rotation of the output shaft or other component of the second motor may drive commensurate rotation of the belt 120.

The belt 120 may also include a plurality of laterally aligned slats 126 connected to the one or more continuous tracks described above. For example, as shown in FIG. 1, each slat 126 may extend substantially parallel to at least one adjacent slat 126. Additionally, each slat 126 may be hingedly, pivotally, and/or otherwise movably coupled to the one or more continuous tracks of the deck 120 via one or more respective couplings. Such couplings may comprise, for example, a bracket, pin, screw, clip, bolt, and/or one or more other fastening components configured to secure a respective slat 126 to the continuous track described above, while allowing the slat 126 to pivot, rotate, and/or otherwise move relative to the track while the belt 120 revolves about the deck 112.

With continued reference to FIG. 1, the exercise machine 102 may also include one or more sidewalls 128 connected to the deck 112. For example, the exercise machine 102 may include a first sidewall 128 on a left-hand side of the deck 112, and a second sidewall 128 on the right-hand side of the deck 112. Such sidewalls 128 may be made from cloth, foam, plastic, rubber, polymers, and/or other like material, and in some examples, the sidewalls 128 may assist in damping and/or otherwise reducing noise generated by one or more of the motors and/or other components of the deck 112.

The exercise machine 102 may also include one or more posts 130 extending upwardly from the deck 112. For example, the exercise machine 102 may include a first post 130 on the left-hand side of the deck 112, and a second post 130 on the right-hand side of the deck 112. Such posts 130 may be made from a metal, alloy, plastic, polymer, and/or other like material, and similar such materials may be used to manufacture the deck 112, the slats 126, and/or other components of the exercise machine 102. In such examples, the posts 130 may be configured to support the display 104, and in some examples, the display 104 may be directly coupled to a crossbar 132 of the exercise machine 102, and the crossbar 132 may be connected to and/or otherwise supported by the posts 130. For example, the crossbar 132 may comprise one or more hand rests or handles useful in supporting the user 106 during exercise. In some examples, the crossbar 132 may be substantially C-shaped, substantially U-shaped, and/or any other configuration. In any of the examples described herein, the crossbar 132 may extend from a first one of the posts 130 to a second one of the posts 130. Further, in some examples, the posts 130 and the crossbar 132 may comprise a single integral component of the upper assembly 110. Alternatively, in other examples, the posts 130 and the crossbar 132 may comprise separate components of the upper assembly 110. In such examples, the upper assembly 110 may include one or more brackets 134, endcaps 136, and/or additional components configured to assist in coupling the one or more posts 130 to the crossbar 132.

As noted above, the exercise machine 102 may also include a hinge, joint, pivot, bracket 138 and/or other suitable mechanism to allow for adjustment of the position or orientation of the display 104 relative to the user 106 whether they are walking, jogging, running, and/or otherwise working out on the exercise machine 102, or working out near or adjacent to the exercise machine 102. For example, such brackets 138 may include at least one component rigidly connected to the crossbar 132. Such brackets 138 may also include one or more additional components rigidly coupled to the display 104. In such examples, the components of the bracket 138 connected to the display 104 may be moveable, with the display 104 relative to the components of the bracket 138 connected to the crossbar 132. Such components may include one or more dove-tail slider mechanism, channels, and/or other components enabling the display 104 to controllably slide and/or otherwise move relative to the crossbar 132. Such components may also enable the user 106 to fix the position of the display 104 relative to the crossbar 132 once the user 106 has positioned the display 104 as desired.

As shown in FIGS. 1 and 2, the exercise machine 102 may also include one or more controls 144, 146 configured to receive input from the user 106. The exercise machine 102 may further include one or more sensors 147 configured to sense, detect, and/or otherwise determine one or more performance parameters of the user 106 before, during, and/or after the user 106 participates in an exercise class using the exercise machine 102. In any of the examples described herein, the controls 144, 146 and the one or more sensors 147 may be operably and/or otherwise connected to one or more controllers, processors, and/or other digital hardware 148 of the exercise machine 102.

The digital hardware 148 (shown in phantom in FIGS. 1 and 2) associated with the exercise machine 102 may be connected to or integrated with the exercise machine 102, or it may be located remotely and wired or wirelessly connected to the exercise machine 102. The digital hardware 148 may include digital storage (e.g., a hard drive or other such memory), one or more processors (e.g., a microprocessor) or other like computers or controllers, communications hardware, software, and/or one or more media input/output devices such as displays, cameras, microphones, keyboards, touchscreens, headsets, and/or audio speakers. In various exemplary embodiments these components may be connected to and/or otherwise integrated with the exercise machine 102. All communications between and among such components of the digital hardware 148 may be multichannel, multi-directional, and wireless or wired, using any appropriate protocol or technology. In various exemplary embodiments, the digital hardware 148 of the exercise machine 102 may include associated mobile and web-based application programs that provide access to account, performance, and other relevant information to users from local or remote exercise machines, processors, controllers, personal computers, laptops, mobile devices, or any other digital device or digital hardware. In any of the examples described herein, the one or more controllers, processors, and/or other digital hardware 148 associated with the exercise machine 102 may be operable to perform one or more functions associated with control logic of the exercise machine 102. Such control logic may comprise one or more rules, programs, or other instructions stored in a memory of the digital hardware 148. For example, one or more processors included in the digital hardware 148 may be programmed to perform operations in accordance with rules, programs, or other instructions of the control logic, and such processors may also be programmed to perform one or more additional operations in accordance with and/or at least partly in response to input received via one or more of the controls 144, 146, via one or more of the sensors 147, and/or via various controls, user interfaces, or other components provided by the display 104. In any of the examples described herein, the display 104 may comprise a touch screen, a touch-sensitive (e.g., capacitance-sensitive) display, and/or any other device configured to display content and receive input (e.g., a touch input, tap input, swipe input, etc.) from the user 106.

In any of the examples described herein, one or more of the controls 144, 146 associated with the exercise machine 102 may comprise an infinity wheel-type control. Such a control may be useful in changing and/or otherwise controlling, for example, the incline of the deck 112, the speed of the belt 120, and/or other parameters of the exercise machine 102 associated with incremental increases or decreases. In an example embodiment, one or more of the controls 144, 146 associated with the exercise machine 102 may include a rotary dial connected to a corresponding rotary encoder. In such examples, the rotary encoder may include one or more detents or other components/structures that may be tuned for a desired incremental change in a corresponding parameter of the exercise machine 102. For example, the rotary encoder may be tuned such that each detent thereof may correlate to a 0.5% increase or decrease in an incline angle of the deck 112. Alternatively, the rotary encoder may be tuned such that each detent thereof may correlate to a 0.1 mph increase or decrease in a speed of the belt 120. In still further examples, percentages, speeds, and/or other increments greater than or less than those noted above may be chosen. Additionally, one or more such controls 144, 146 may include one or more additional buttons, wheels, touch pads, levers, knobs, or other components configured to receive additional inputs from the user 106, and such additional components may provide the user 106 with finer control over the corresponding parameters of the exercise machine 102. One or more such controls 144, 146 may also include a respective control housing configured to assist in mounting the control 144, 146 to the crossbar 132 or other components of the exercise machine 102.

With continued reference to FIGS. 1 and 2, in various example embodiments, the one or more sensors 147 of the exercise machine 102 may be configured to sense, detect, measure, and/or otherwise determine a range of user data, parameters of the exercise machine 102, and/or other information, from both the exercise machine 102 and the user 106, instantaneously and/or over time. For example, the exercise machine 102 may include one or more sensors 147 that measure the incline of the deck 112, the speed of the belt 120, a load applied to the deck 112, the belt 120, one or more of the motors described above, and/or other components of the exercise machine 102, an amount of energy expended by the user 106, a power output of the exercise machine 102, user weight, steps, distance, total work, repetitions, an amount of resistance applied to the belt 120 by one or more of the motors described above and/or other components of the exercise machine 102, a pedal cadence, a brake force or resistance, as well as any other information associated with, for example, a treadmill, a stationary bicycle, or other exercise machine 102. The exercise machine 102 may also include sensors 147 to measure user heart-rate, respiration, hydration, calorie burn, or any other physical performance metrics, or to receive such information from sensors provided by (e.g., worn by) the user 106. Where appropriate, such information can be calculated as current/instantaneous values, maximum, minimum, average, or total over time, or using any other statistical analysis. Trends can also be determined, stored, and displayed to the user, the instructor, and/or other users. Such sensors 147 may communicate with memory and/or processors of the digital hardware 148 associated with the exercise machine 102, nearby, or at a remote location, using wired or wireless connections. Such sensors 147 and/or the processors of the digital hardware 148 may also communicate with one or more processors disposed remote from the exercise machine 102 using such wired or wireless connections.

In various exemplary embodiments, the exercise machine 102 may also include one or more indicators (not shown) to provide information to the user 106. Such indicators may include lights, projected displays, speakers for audio outputs, or other output devices capable of providing a signal to a user 106 to provide the user 106 with information such as timing for performing an exercise, time to start or stop exercise, or other informational indicators. For example, such indicators (e.g., lights or projected displays) could display information regarding the number of sets and repetitions performed by the user 106 at a location where it can be seen by the user 106 during the performance of the relevant exercise.

With reference to FIG. 2, and as noted above, the display 104 of the exercise machine 100 may comprise and/or may be driven by a user input device such as a touchscreen, mouse, voice control, or other suitable input device. In some examples, the display 104 or at least a portion thereof, may comprise a touchscreen configured to receive touch input from the user 106. The display 104 may be any size, but optimally are large enough and oriented to allow the display of a range of information including one or more video streams, a range of performance metrics corresponding to the user 106, a range of additional performance metrics associated with one or more additional users exercising on exercise machines remote from the exercise machine 102, and a range of different controls. In various exemplary embodiments, the display 104 may include some or all of its area that can reflect the image of the user 106 to provide user feedback regarding their form and performance of various activities.

In various exemplary embodiments the user 106 can use the display 104 or one or more user interfaces 200 displayed on the display 104 to selectively present a range of different information including live and/or archived video, performance data, and other user and system information. In any of the examples described herein, such user interfaces 200 can provide a wide range of control and informational windows that can be accessed and removed individually and/or as a group by a click, touch, voice command, or gesture. In various exemplary embodiments, such windows may provide information about the user's own performance and/or the performance of other participants in the same exercise class both past and present.

Example user interfaces 200 presented via the display 104 may be used to access member information, login and logout of the system 100, access live content such as live exercise classes and archived classes or other content. User information may be displayed in a variety of formats and may include historical and current performance and account information, social networking links and information, achievements, etc. The user interfaces described herein can also be used to access the system 100 to update a user profile (e.g., a user profile that is unique to the user 106) or member information, manage account settings such as information sharing, and/or to modify one or more settings of a control included in the user interface 200.

An example user interface 200 may also be presented on the one or more displays 104 to allow users to manage their experience, including selecting information to be displayed and arranging how such information is displayed on the display 104. Such a user interface 200 may present multiple types of information overlaid such that different types of information can be selected or deselected easily by the user 106. For example, performance metrics and/or other information may be displayed over video content using translucent or partially transparent elements so the video behind the information elements can be seen together with (i.e., simultaneously with) the performance metrics and/or other information itself. Further, example user interfaces 200 may present a variety of screens to the user 106 which the user 106 can move among quickly using the provided user input device, including by providing a touch input via the display 104.

In any of the examples described herein, the processor and/or other components of the digital hardware 148 may control the display 104 and/or otherwise cause the display 104 to display the various user interfaces 200 of the present disclosure. For example, the processor or other components of the digital hardware 148 may cause the display 104 to display a user interface 200 comprising a home screen that provides basic information about the system 100 and/or the exercise machine 102, as well as available options. Such a home screen may provide direct links to information such as scheduled classes, archived classes, a leaderboard, instructors, and/or profile and account information. The home screen may also provide direct links to content such as a link to join a particular class. The user 106 can navigate among the different portions of the home screen by selecting such links using the applicable input device such as by touching the display 104 at the indicated location, or by swiping to bring on a new screen. An example user interface 200 providing such a home screen may also provide other information relevant to the user 106 such as social network information, and navigation buttons that allow the user to move quickly among the different screens in the user interface 200.

In various example embodiments, one or more of the user interfaces 200 may include various components configured to provide information to the user 106 while the user 106 is participating in an exercise class. For example, as will be described in greater detail below, one or more example user interfaces 200 may include a timeline 202 (e.g., a segmented timeline) indicating portions of an exercise class being displayed on the display 104, and a position and/or location within the timeline corresponding to the current portion of the exercise class being displayed. An example user interface 200 may also include a scorecard 204, leaderboard, or other component providing rankings, output, exercise machine parameters, user data, and/or other information related to other users participating in (either in real time, or previously) the exercise class being displayed on the display 104. An example user interface 200 may further include various display bars 206 or other components providing performance metrics, performance information, and/or other user data associated with the user 106. Such information may include, for example, various settings or other parameters of the exercise machine 102 (e.g., a current incline of the deck 112, a current speed of the belt 120, a current pedal cadence of a stationary bicycle, a current braking force or resistance of the stationary bicycle, etc.), an output of the user 106, and/or other information corresponding to the user 106 participating in an exercise class. Additionally, in some examples the user interface 200 may include one or more executable controls 210 operable to modify an incline of the deck 112, a speed of the belt 120, a pedal cadence of a stationary bicycle, a braking force or resistance of the stationary bicycle, and/or other parameters of the exercise machine 102 while the user 106 is participating in an exercise class. As shown in at least FIG. 2, in such embodiments the timeline 202, scorecard 204, leaderboard, display bars 206, executable controls 210, and/or other components of the user interface 200 may be displayed on the display 104 together with (e.g., simultaneously with) content 208 comprising the exercise class that the use 106 is currently participating in.

In various exemplary embodiments, the user interfaces 200 described herein may be run through a local program or application using a local operating system such as an Android or iOS application, or via a browser-based system. Any of the performance metrics or other information described herein with respect to the various user interfaces 200 may also be accessed remotely via any suitable network such as the internet. For example, users 106 may be able to access a website from a tablet, mobile phone, computer, and/or any other digital device, and such users 106 may be able to review historical information, communicate with other participants, schedule classes, access instructor information, and/or view any of the information described herein with respect to the various user interfaces 200 through such a website.

Figure 3:
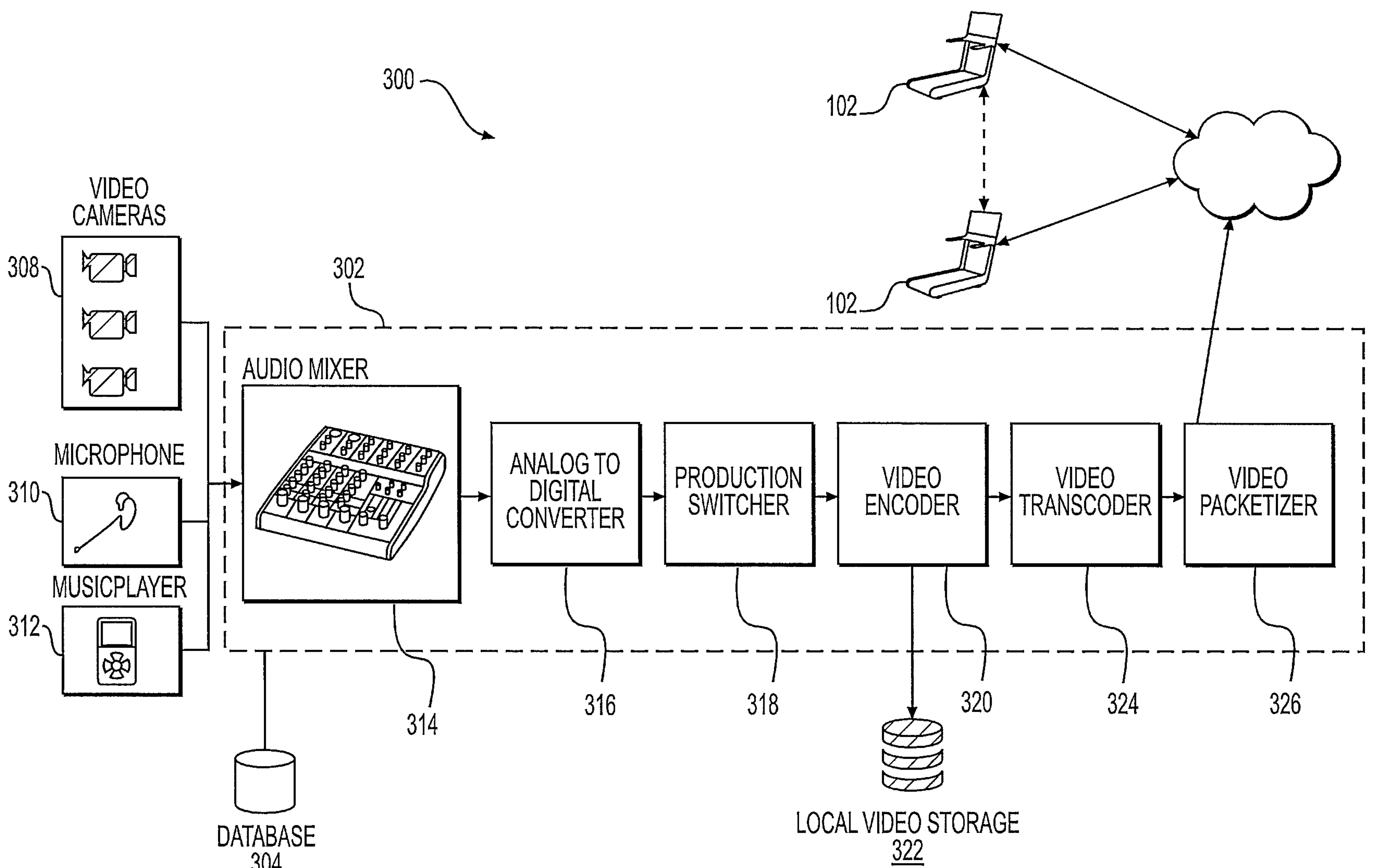
FIG. 3 is a schematic illustration showing exemplary components used for content creation and/or distribution.

FIG. 3 illustrates an example networked exercise system 300 of the present disclosure including one or more exercise machines 102 that are in communication via an example network. Such an example networked exercise system 300 may be used to, for example, capture and/or otherwise generate audio content, video content, and/or other content corresponding to an exercise class being performed by one or more instructors. The networked exercise system 300 may also be configured to generate a video file and/or any other electronic file, digital file, or the like comprising the captured audio content and video content. In some examples, the networked exercise system 300 may also be configured to generate one or more of the executable controls 210 described herein with respect to the user interface 200 (FIG. 2), and to associate such executable controls with the video file such that playback of at least part of the video file by a processor of an exercise machine 102 (e.g., via a display 104 of the exercise machine 102) may result in the display of the executable control 210.

In further examples, the networked exercise system 300 may also be configured to provide a video file (e.g., a video file including content associated with an exercise class) to a plurality of exercise machines, and to receive corresponding user data from the plurality of exercise machines. For instance, such user data may include respective settings associated with a common performance metric, and the respective settings may comprise settings selected and/or otherwise used by users on the plurality of exercise machines during playback of a particular part of the video file. In such examples, a processor, server, or other component of the networked exercise system may identify a timestamp associated with the particular part of the video file. In such examples, the processor, server, or other component may also generate an executable control corresponding to the performance metric, and may generate an additional video file that includes the content associated with the exercise class, and the executable control. In such examples, playback of the additional video file may cause display of the executable control at a part of the additional video file corresponding to the timestamp described above. In any of the examples described herein, content captured and/or distributed by the networked exercise system 300 may comprise live and/or archived exercise classes, live and/or archived instructional content such as video content explaining how to properly perform an exercise, scenic or map-based content, videos, and/or animations that can be rendered in three-dimensions from any angle may be created and stored in various local or remote locations and shared across the networked exercise system 300.

In various example embodiments, the networked exercise system 300 may be managed through one or more networked backend servers 302 and may include various databases 304 for storage of user data, system information, performance information, archived content, etc. Example local systems 100 (FIG. 1) may be in communication with the networked backend servers 302 via any appropriate network 306 (e.g., a content distribution network 306), including without limitation, the internet. As an example of an alternative distribution approach, in various exemplary embodiments the backend servers 302 could be eliminated and data could be communicated throughout the system in a distributed or peer-to-peer manner rather than via a central server network. In such a networked exercise system 300, user data (e.g., performance data) may be broken up into small packets or "pieces" and distributed among user devices such that complete data sets are quickly distributed to all devices for display as required.

Content for distribution through the network 306 can be created in a variety of different ways. Content recording locations may include professional content recording studios, amateur and home-based locations, gyms, etc. In various exemplary embodiments, recording studios may include space for live instructor-led exercise classes with live studio participation, or may be dedicated studios with no live, in-studio participation. As shown in FIG. 3, recording equipment including one or more video cameras 308, microphones 310, mp3 players or other music players 312, and/or other components and can be used to capture the instructor and/or participants during the class. Multiple cameras 308 can provide different views, and 3D cameras 308 can be used to create 3D content. In various exemplary embodiments, content may also be generated locally by users 106. For example, exercise machines 102 may be equipped with recording equipment including microphones 310 and cameras 308. Users 106 may generate live or recorded classes that can be transmitted, stored in or by the networked exercise system 300, and distributed via the network 306.

With continued reference to FIG. 3, class content (e.g., audio content and/or video content) may be generated by providing outputs of the one or more video cameras 308, microphones 310, and/or music players 312 as inputs to an audio mixer 314. The audio mixer 314 may output content to an analog to digital converter 316, which may provide converted data to a production switcher 318. The production switcher 318 may send the production video to a video encoder 320, which may store the encoded video to a local storage device 322, and may also send it to a video transcoder 324.

In some examples, the video encoder 320 may receive input from one or more users of the backend servers 302 comprising a command to associate an executable control 210 with the video file being created by the networked exercise system 300. In such examples, the video encoder 320 may tag, save, embed, and/or otherwise associate such an executable control 210 with the video file, and at a desired location within the video file. Such a desired location may comprise and/or correspond to a timestamp associated with the input and/or associated with a particular part of the video file. Alternatively, the video encoder 320 and/or other components of the backend servers 302 may identify a verbal command from an instructor that is leading an exercise class. In such examples, the video encoder 320 and/or other components of the backend servers 302 may identify the verbal command included in audio content received from a microphone 310 and/or from a video camera 308. Such a command may correspond to a parameter of an exercise machine 102 (e.g., an incline of the deck 112, a speed of the belt 120, a pedal cadence of a stationary bicycle, a braking force or resistance of the stationary bicycle, etc.). Additionally or alternatively, such a command may correspond to any other performance metric or parameter (e.g., a power zone, a stride type, a position of a seat associated with the exercise machine102, a stretching technique or form, etc.) associated with the exercise class being performed by the instructor. In such examples, the video encoder 320 and/or other components of the backend servers 302 may identify a timestamp associated with the command (e.g., a timestamp in the video content and/or the audio content corresponding to the command). In such examples, the video encoder 320 and/or other components of the backend servers 302 may associate the executable control 210 with the video file by linking the executable control 210 to a part of the video file corresponding to the timestamp.

Additionally in any of the examples described herein, the video encoder 320 and/or other components of the backend servers 302 may identify such a verbal command via natural language processing software or techniques. As will be describe in greater detail below, in still further examples, one or more such executable controls 210 may be generated based at least in part on user data received from a plurality of exercise machines 102. In such examples, such user data may include respective settings associated with a common performance metric. For instance, such respective settings may be used on the plurality of exercise machines 102 during playback of a particular part of a video file comprising an exercise class (e.g., an archived exercise class or a live/real-time exercise class). In such examples, the video encoder 320 and/or other components of the backend servers 302 may identify a timestamp associated with the particular part of the video file, and may generate an executable control corresponding to the common performance metric noted above. In some such examples, the video encoder 320 and/or other components of the backend servers 302 may also generate an additional (e.g., a second) video file that includes audio and video content of the exercise class, as well as the executable control. Playback of such an additional video file may cause display of the executable control at a part of the additional video file corresponding to the timestamp.

Further, the video transcoder 324 may output transcoded data to a video packetizer 326, which may then send a packetized data stream out through the network 306 to remote users 106. In various exemplary embodiments, instructors and/or users 106 may be provided with access to a content creation platform that they can use to help them create content. Such a platform may provide tools for selecting and editing music, managing volume controls, pushing out chat or other communications to users 106.

As described above with respect to FIGS. 1 and 2, through the display 104 and/or other user interface on their exercise machine 102, users 106 may access lists, calendars, and schedules of live and recorded exercise classes available for delivery through the display 104. In various exemplary embodiments, once the user 106 selects an exercise class, the local system 100 may access and/or display a primary data stream for the class. This primary data stream may include video, music, voice, text, or any other data, and may represent a live or previously recorded exercise class. The local system 100 may be equipped for hardware video accelerated encoding/decoding to manage high definition video quality at up to 1080 pixels based on existing technology. The local system 100 may automatically adjust bitrate/quality of the data stream for the class in order to bring participant the highest quality video according to user's bandwidth/hardware limitations.

In various exemplary embodiments, networked exercise systems 300 and methods of the present disclosure may include multi-directional communication and data transfer capabilities that allow video, audio, voice, and data sharing among all users 106 and/or instructors. This allows users 106 to access and display multi-directional video and audio streams from the instructor and/or other users regardless of location, and to establish direct communications with other users 106 to have private or conferenced video and/or audio communications during live or recorded classes. Such data streams can be established through the local system 100 for presentation via the one or more displays 104 via one or more of the user interfaces 200 described above. In various exemplary embodiments, users 106 can manage multiple data streams to select and control inputs and outputs. The local system 100 may allow the user 106 to control the volume of primary audio stream for the class as well as other audio channels for different users or even unrelated audio streams such as telephone calls or their own music selections. For example, this would allow a user 106 to turn down the instructor volume to facilitate a conversation with other users.

For live classes, in various exemplary embodiments the instructor may have the ability to communicate with the entire class simultaneously or to contact individual users, and solicit feedback from all users regardless of location in real-time. For example, instructors could ask users verbally, or text a pop-up message to users 106, seeking feedback on difficulty level, music choice, terrain, etc. Users 10 6 could then respond through components of the local system 100 by selecting an appropriate response, or providing verbal feedback. This allows instructors to use crowdsourcing to tailor a class to the needs of the participants, and to improve their classes by soliciting feedback or voting on particular class features or elements. In any of the examples described herein, one or more of the executable controls described herein may comprise such a text or pop-up message to users 106 seeking feedback, providing guidance or encouragement, providing further instructions related to the exercise class, and/or providing any other information.

In various exemplary embodiments, instructors may also be able to set performance targets, and the system can measure and display to the user 106 and the instructor their performance relative to the target. For example, the instructor may set target metrics e.g. target power and speed, then display this next to users' readings with a color coding to indicate whether or not the user is meeting this target. The system may allow the instructor to remotely adjust exercise machine settings for individual users 106. In various exemplary embodiments, the exercise machine 102 may also automatically adjust based on information from the user 106, the instructor, or based on performance. For example, the exercise machine 102 may adjust the difficulty to maintain a particular performance parameter such as heart rate within a particular range or to meet a particular performance target. Any of the executable controls described herein may be generated and/or configured to modify a parameter of the exercise machine 102 in order to assist the user 106 in meeting and/or exceeding such performance goals or targets.

With continued reference to FIG. 3, in various exemplary embodiments, the networked exercise system 300 described herein may allow users 106 to create accounts (e.g., user profiles) and save and manage their user data (e.g., performance data). As discussed above, the system may allow users 106 to browse schedules for upcoming live classes, signup for future live streaming classes, and setup reminders. Users 106 may also be able to invite others to participate in a live class, and setup text, email, voice, or other notifications and calendar entries. Users 106 may be able to access system, account, performance, and all other data via web-based or application based interfaces for desktop and/or mobile devices, in addition to the user interface for the local system 100 associated with their exercise machine 102.

In various exemplary embodiments, the networked exercise system 300 can provide for simultaneous participation by multiple users in a recorded class, synchronized by the system and allowing access to all of the same communication and data sharing features that are available for a live class. With such a feature, the participants simultaneously participating in the same archived class can compete against each other, as well as against past performances or "ghost" participants for the same class. In some of the examples described herein, one or more executable controls may be generated and/or configured to modify a parameter of the exercise machine 102 in order to assist the user 106 in keeping pace with such past performances, "ghost" participants, and/or other performance goals or targets.

In some examples, the networked computer system 300 may be configured to feed synchronized live and/or archived video content and live and/or archived sensor data to users over the network 306. In various exemplary embodiments, and as illustrated in FIG. 3, the networked exercise system 300 may be configured with a plurality of user exercise machines 102 in communication with the video content distribution network 306. The user exercise machines 102 may also be in communication with various other networks and servers. Additionally, in any of the examples described herein, a control station (not shown) may provide signals via the network 306 to control the collection, storage, and management of data (e.g., user data, video content, audio content, parameters of the various exercise machines 102, etc.) across the networked exercise system 300.

Figure 4:
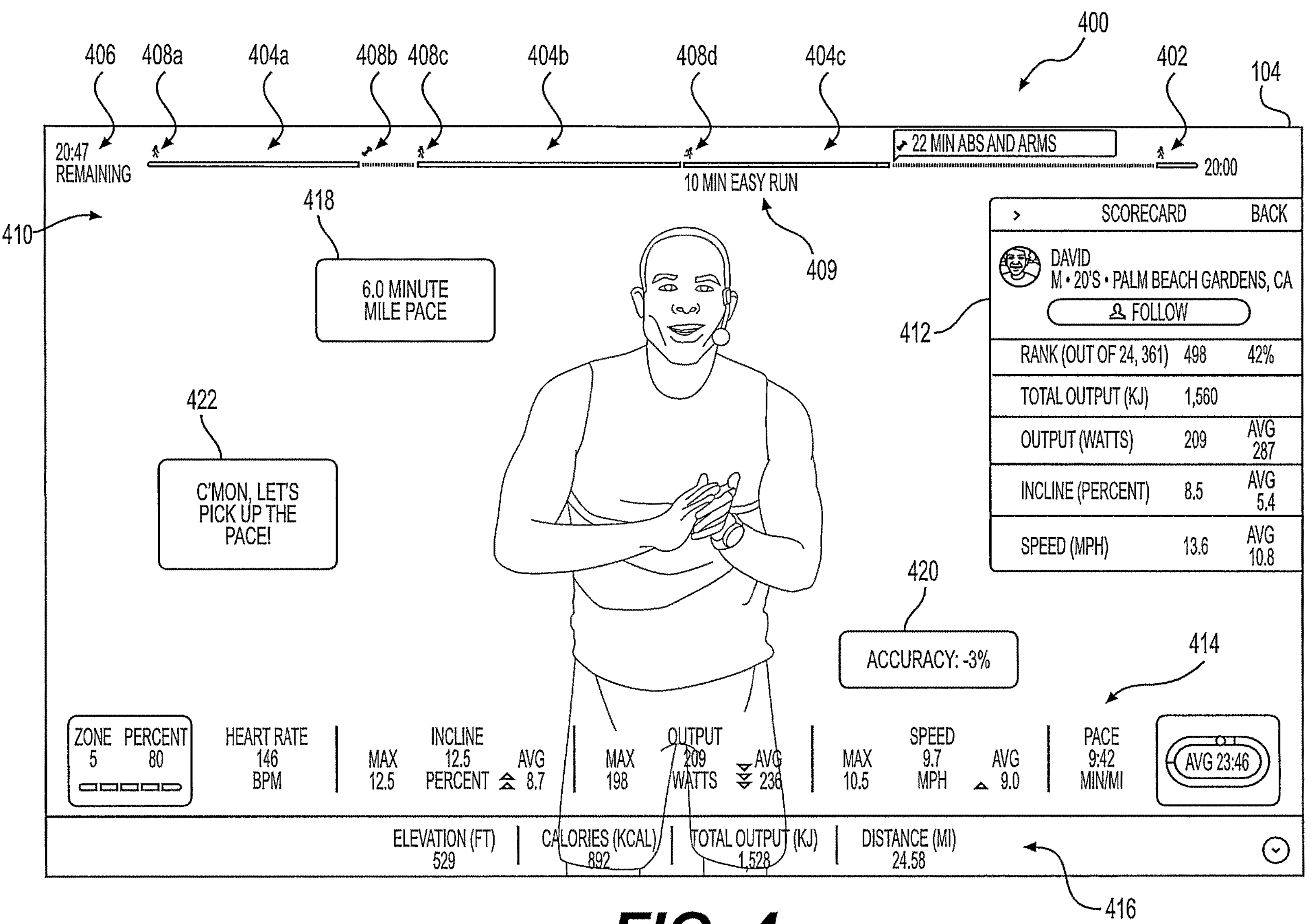
FIG. 4 illustrates an example user interface of the present disclosure showing video content corresponding to an exercise class, as well as a scorecard.

FIG. 4 illustrates an example user interface 400 of the present disclosure, and the user interface 400 may be similar to and/or the same as the user interface 200 described above with respect to FIG. 2. In such examples, the user interface 400 may be provided to the user 106 during a selected exercise class. When an exercise class is being displayed, played back, and/or otherwise provided via the one or more displays 104 through the user interface 400, in various exemplary embodiments the primary video feed may be shown as the background video full-screen or in a sub-window on the display 104. Information elements may be provided on different parts of the display screen to indicate any performance metrics, including total time, elapsed time, time left, distance, speed (e.g., speed of the belt 120), mile pace of the user 106, incline (e.g., incline of the deck 112), elevation, resistance, braking force, power, total work, energy expended (e.g., output), cadence (e.g., pedal cadence), power zone, heart rate, respiration, hydration, calorie burn, and/or any custom performance scores that may be developed. The displayed information may also include the trend or relationship between different performance metrics. For example, the display 104 can indicate a particular metric in a color that indicates current performance compared to average performance for an exercise class or over time, such as red to indicate that current performance of the user 106 is below average or green to indicate above average performance. Trends or relative performance can also be shown using color and graphics, such as a red down arrow to show that current performance is below average. The displayed information may further include settings, parameters, or other information (e.g., actual settings or settings requested by the instructor) related to the activity being performed during one or more segments of the exercise class (e.g., a setting or position of a seat of the exercise machine 102, a stride type, a stretch position or form, etc.).

In various exemplary embodiments, the display 104 may also display information that supports or supplements the information provided by the instructor. Examples include one or more segmented timelines 402 that are illustrated together with at least part of the selected exercise class in the user interface 400. As shown in at least FIGS. 4 and 5, an example segmented timeline 402 may include one or more segments 404*a*, 404*b*, 404*c* . . . 404*n* (collectively, "segments 404") corresponding to respective portions, parts, or other exercise segments of the selected exercise class. The size, length, width, height, relative position, color, opacity, and/or other configurations of such segments 404 may be representative of, for example, the length of the corresponding portions or parts of the selected exercise class. The segmented timeline 402 may also provide an indication 406 of elapsed time and/or remaining time for the present workout segment and/or for the exercise class generally. The segmented timeline 402 may also include one or more visual indica 408*a*, 408*b*, 408*c* . . . 408*n* (collectively, "indicia 408") indicating an activity requirement (e.g., run, jog, sprint, lift weights, etc.), an equipment requirement (e.g., dumbbells), and/or other requirement associated with a respective exercise segment of the selected exercise class. For example, the indicia 408*a* may indicate that the segment 404*a* comprises a walking segment, indicia 408*d* may indicate that the segment 404*c* comprises a running segment, and the indicia 408*b* may indicate that weights are required for at least part of the segment 404*a*. In any of the examples described herein, such segmented timelines 402 may also include one or more lists or windows identifying and/or describing upcoming workout segments or features, instructional information such as graphics or videos demonstrating how to properly perform exercises, or other information relevant to the exercise class in progress. Such segmented timelines 402 may also provide and/or otherwise include information 409 indicating the current segment of the exercise class and/or the current activity that the instructor is requesting the user 106 perform.

As shown in at least FIG. 4, the user interface 400 may include a primary window 410 configured to show the live or archived exercise class or other content that the user 106 selected. In various exemplary embodiments, the user interface 400 may further include one or more performance metric windows 412 (e.g., the "scorecard" illustrated in FIG. 4) overlaid on and/or otherwise displayed together with the primary window 410. Such performance metric windows 412 may show a ranking, total output, current output, incline, belt speed, mile pace, one or more averages of such performance metrics, and/or other specific performance metrics for the user's current class, past classes, or other performance information. Such performance metric windows 412 may be presented anywhere on the display 104, and may be user selectable such that they can be displayed or removed by a screen touch or gesture.

The user interface 400 may also allow the user 106 to toggle between display of maximum, average, and total results for different performance metrics. Additionally, the user interface 400 may allow the user 106 to hide or display information elements, including performance metrics, video streams, user information, etc. all at once or individually. Performance metrics and/or other performance information can also be displayed in various display bars 414, 416 that can be hidden or displayed as a group or individually. The user interface 400 may provide for complete controls for audio volume, inputs, and outputs as well as display output characteristics.

In any of the examples described herein, the user interface 400 may also include one or more executable controls 418. Such executable controls 418 may be executable by a processor of the digital hardware 148 upon playback of a video file comprising audio and/or video content of an exercise class. For instance, upon playback of such a video file, the processor of the digital hardware 148 may provide one or more such executable controls 418 during particular portions of the exercise class at which an instructor utters and/or otherwise provides a corresponding performance command. In any of the examples described herein, such executable controls 418 may correspond to the performance command uttered by the instructor and may comprise visual indicia (e.g., text, images, etc.) indicating, embodying, and/or otherwise corresponding to the performance command. In such examples, such executable controls 418 may comprise pop-up messages or other means by which the instructor may enhance engagement with exercise class participants. In this way, such executable controls may effectively convey performance commands, a desired performance parameter/metric, words of encouragement, guidance, instructions, and/or other information to exercise class participants. In some examples, such executable controls 418 may comprise text windows, images, pop-up boxes, graphics, icons, or other visual content that may not be configured to receive an input (e.g., a touch input) from the user 106.

In other examples, on the other hand, one or more executable controls 418 of the present disclosure may be configured to receive an input (e.g., a touch input) from the user 106. In such examples, an executable control 418 may be operable to modify a parameter of the exercise machine 102 while the user 106 is participating in an exercise class. For example, such an executable control 418 may be configured to modify a speed of the belt 120 in accordance with a desired speed or pace identified by the instructor. In further examples, one or more executable controls 418 of the present disclosure may be configured to modify an incline of the deck 112, a resistance associated with the belt 120, a pedal cadence of a stationary bicycle, a braking force or resistance of the stationary bicycle, and/or other parameters of the exercise machine 102. For example, in embodiments in which the exercise machine 102 comprises a treadmill, the user interface 400 may include one or more relatively specific and/or relatively descriptive executable controls 418 indicating a particular setting of the exercise machine 102 that will be implemented in response to an input received via the executable control 418. For instance, the relatively specific and/or relatively descriptive executable control 418 shown in FIG. 4 indicates that upon receipt of an input via the executable control 418, the speed of the belt 120 will be adjusted to obtain a 6.0 minute mile pace. In other examples, on the other hand, one or more executable controls 418 provided by the user interface 400 may be relatively vague, nebulous, or nondescript. For instance, in some embodiments the user interface 400 may include a relatively vague "jog" executable control 418, a "run" executable control 418, a "sprint" executable control 418, and/or other executable controls that do not specify a particular setting of the exercise machine 102. Similar to the executable control 418 illustrated in FIG. 4, such relatively vague executable controls may be configured to receive one or more inputs from the user 106 while the user 106 is participating in an exercise class using the exercise machine 102, and may be operable to modify the speed of the belt 120 and/or other settings or parameters of the exercise machine 102 based at least in part on such an input.

For instance, a relatively vague "jog" executable control 418 may be associated with a first speed of the belt 120 such that, upon receipt of a touch input via the executable control 418, the processor, and/or other digital hardware 148 of the exercise machine 102 may control the motor of the deck 112 driving the belt 120 to cause the belt 120 to rotate about the deck 112, at a speed corresponding to a jogging pace of the user 106. In some examples, the speed associated with the relatively vague "jog" executable control 418 may be a default jogging pace stored in a memory of the digital hardware 148 and/or otherwise associated with the executable control 418. Alternatively, in other examples the speed associated with the relatively vague "jog" executable control 418 may be customized, programmed, entered, and/or otherwise selected by the user 106, when establishing a user profile unique to the user 106, before the user 106 begins participating in the current exercise class, while the user 106 is participating in the exercise class, and/or at any other time. Accordingly, in such examples the user 106 may select a speed at which the user 106 desires the belt 120 to rotate when the user selects and/or otherwise, provides a touch input via the "jog" executable control 418. In such examples, the speed of the belt 120, and/or other parameter of the exercise machine 102 associated with the "jog" executable control 418 may be stored as part of the user profile of the user 106 in the memory associated with the digital hardware 148 and/or in, for example, the database 304 and/or other memory associated with the one or more servers 302 of the system 300 (FIG. 3).

In still further examples, the speed associated with the relatively vague "jog" executable control 418 may be a speed that is identified, calculated, selected, and/or otherwise determined by, for example, the processor of the exercise machine 102, and/or a processor or other component of the one or more servers 302. In such further examples, the speed associated with the "jog" executable control 418 may be determined based on, for example, aggregate user data associated with past user selections, past user performances, or other previous workouts of the user 106. In such examples, for instance, the processor and/or other digital hardware 148 of the exercise machine 102 may sense, collect, and/or otherwise determine user data including belt speeds that the user 106 commonly selects during participation in exercise classes using the exercise machine 102. In such examples, the processor, and/or other digital hardware 148 of the exercise machine 102 may store such user data in a memory associated with the digital hardware 148. The processor may also select, identify, and/or otherwise determine a belt speed frequently selected by the user 106 based at least in part on such user data, and may associate the selected speed with the "jog" executable control 418. For instance, such a selected speed may be associated with a warm-up period/segment of previous exercise classes participated in by the user 106, and such a speed may comprise a speed most frequently selected by the user 106 during such previous warm-up periods/segments.

In further examples, a speed of the belt 120 corresponding to such a relatively vague "jog" executable control 418 may be selected and/or indicated by the instructor of the exercise class either prior to the exercise class or during performance of the exercise class. In such examples, the one or more servers 302 may associate such a speed with the executable control 418 during generation of the executable control 418. In still further examples, the speed of the belt 120 corresponding to such a "jog" control may comprise a mean, median, or mode belt speed included in user data received from a plurality of exercise machines 102 during one or more previous playbacks of the exercise class. It is understood that a "run" executable control 418, a "sprint" executable control 418, and/or any other relatively vague, nebulous, or nondescript executable controls 418 described herein may be configured in a similar fashion.

Relatively specific executable controls 418, on the other hand (such as the executable control 418 illustrated in FIG. 4), may include one or more settings that correspond to a specific performance command uttered by the instructor during the exercise class, one or more settings included in user data received from a plurality of exercise machines 102, stored settings (e.g., settings stored in one or more user profiles), and/or settings based at least in part on information received from one or more additional sources. Further, although not illustrated in FIG. 4, it is understood that the user interface 400 may additionally or alternatively include one or more additional executable controls configured to modify an incline of the deck 112, a pedal cadence, a power zone, a braking resistance, a belt resistance, and/or other parameters of the exercise machine 102. In particular, such example executable controls may be configured to receive one or more inputs from the user 106 while the user 106 is participating in an exercise class using the exercise machine 102, and such executable controls may be operable to modify the corresponding parameter of the exercise machine 102 based at least in part on such an input. One or more such executable controls may be configured through a process similar to that described above with respect to the executable control 418.

Additionally, as noted above, any of the processes described herein with respect to configuring, generating, providing, causing the display of, and/or modifying one or more of the executable controls 418 of the present disclosure may be performed locally at the exercise machine 102 by the processor of the digital hardware 148, remote from the exercise machine 102 by one or more processors of the server 302, and/or by the processor of the digital hardware 148 operating in communication and/or in conjunction with one or more processors of the server 302.

With continued reference to FIG. 4, in some examples the user interface 400 may include one or more additional windows 420, 422 and/or other portions configured to provide additional information to the user 106 during an exercise class. For example, in some embodiments the server 302 and/or the processor of the digital hardware 148 may receive user data collected while one or more of the executable controls 418 are displayed via the user interface 400. In such examples, the received user data may include a first setting of the exercise machine 102 selected by the user 106 during a particular part of an exercise class being participated in using the exercise machine 102. In such examples, the server 302 and/or the processor of the digital hardware 148 may determine a difference between such a first setting and a second setting of the displayed executable control 418. The server 302 and/or the processor of the digital hardware 148 may also determine an accuracy metric based at least in part on the difference, and may provide the accuracy metric via, for example, one or more of the windows 420, 422 of the user interface 400 shown on the display 104.

In such examples, an accuracy metric may comprise any number (e.g., a difference, an average, a mode, a median, etc.), parameter, or other indicator of how accurately or inaccurately the user 106 is following the performance command corresponding to the executable control 418. Such an example accuracy metric (e.g., -3%) is shown in the window 420. Additionally or alternatively, such an accuracy metric may comprise one or more graphics, images, figures, colors, flashing schema, or other visual indicia included in the window 420 to provide an indication of how accurately or inaccurately the user 106 is following the performance command corresponding to the executable control 418.

In some examples, one or more of the windows 420, 422 included in the user interface 400 may also include, encouraging messages, explanations, comments, questions, dialogue (e.g., closed captioning), notifications, and/or other information provided by the instructor during the exercise class. Such an example encouraging message (e.g., "C'mon, let's pick up the pace!") is shown in the window 422. Such a window 422 may also be configured to provide one or more notifications to the user 106 based at least in part on the accuracy metric described above. In some examples, such a window 422 may or may not be configured to receive an input (e.g., a touch input) from the user 106. Such an example window 422 may be formed by any of the processes described above with respect to, for example, the executable control 418. For example, the video encoder 320 and/or other components of the backend servers 302 may identify a verbal command from an instructor that is leading an exercise class. In such examples, the video encoder 320 and/or other components of the backend servers 302 may identify a verbal command, a message, a suggestion, an instruction, or other such utterance included in audio content received from a microphone 310 and/or from a video camera 308. Such an utterance may correspond to a parameter of an exercise machine 102, or alternatively, such an utterance may correspond to any other non-performance metric-based message associated with the exercise class being performed by the instructor. In such examples, the video encoder 320 and/or other components of the backend servers 302 may associate a window 422 providing such a message with a video file comprising the exercise class. In any of the examples described herein, the video encoder 320 and/or other components of the backend servers 302 may identify such a message via natural language processing software or techniques. Alternatively, in further examples, an operator of the system 300 may use the video encoder 320 and/or the server 302 to generate the window 422 manually.

Figure 5:
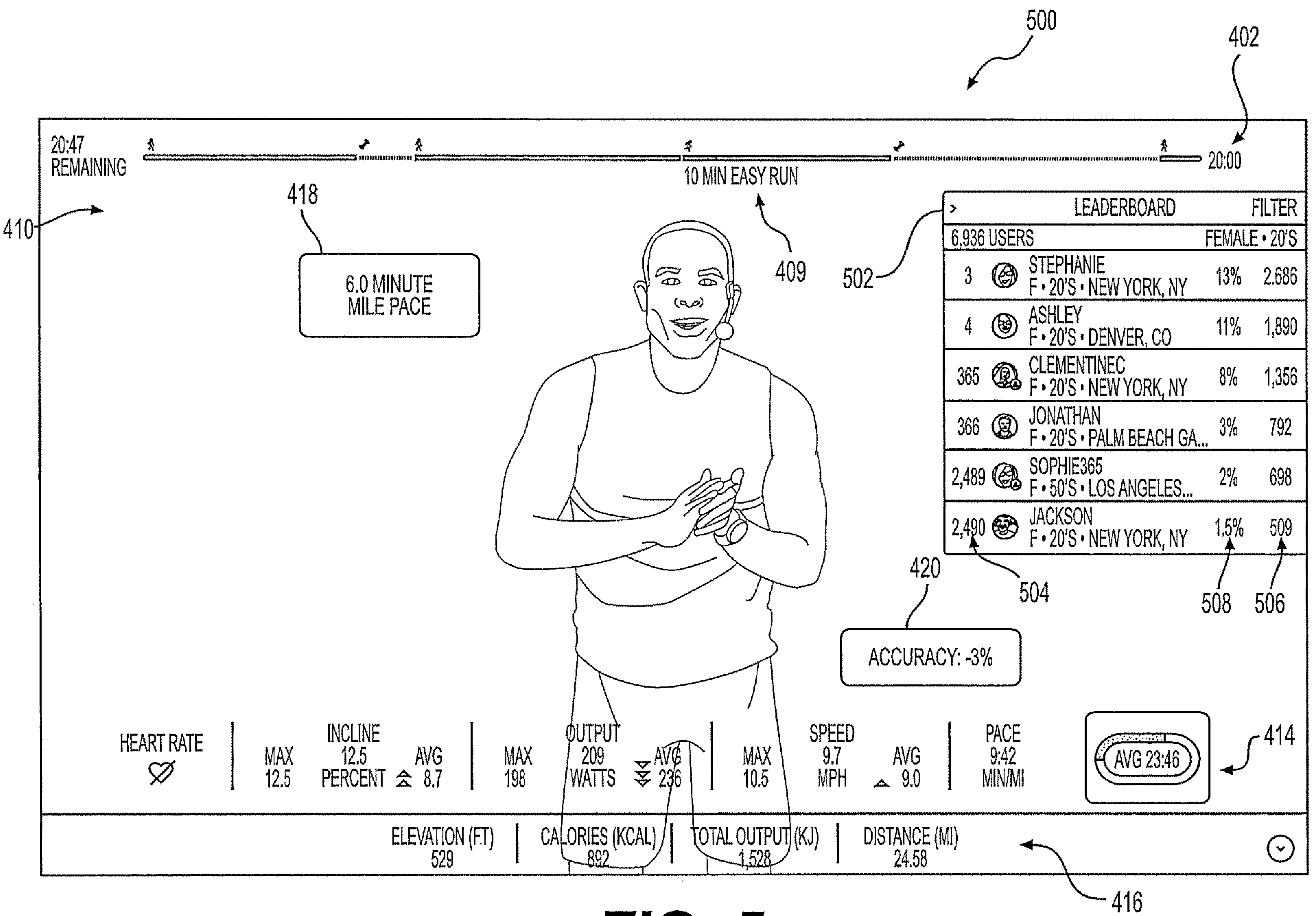
FIG. 5 illustrates another example user interface of the present disclosure showing video content corresponding to an exercise class, as well as a leaderboard.

FIG. 5 illustrates another example user interface 500 of the present disclosure. In such examples, the user interface 500 may be substantially similar to the user interface 400 described above with respect to FIG. 4 and/or may be substantially similar to the user interface 200 described above with respect to FIG. 2. As shown in FIG. 5, such an example user interface 500 may include, among other things, a leaderboard 502 that is displayed so as to allow the user 106 to see his or her performance in comparison to other users participating in the same exercise class. In various exemplary embodiments, a leaderboard 502 may comprise a separate window overlaid on and/or otherwise displayed together with the primary window 410. An example leaderboard 502 may be configured to display the relative performance of all participants, and/or of one or more subgroups of participants. For example, the user 106 may be able to select a leaderboard 502 that shows the performance of participants in a particular age group, male participants, female participants, male participants in a particular age group, participants in a particular geographic area, etc. For instance, in the example shown in FIG. 5, the leaderboard 502 has been configured to show the performance of a group of female participants in their 20's. Users 106 may have the ability to individually curate and/or otherwise configure a leaderboard 502, or have the local system 100 curate a leaderboard 502 by selecting an appropriate group of participants relative to the user 106. Users 106 may be able to curate their own leaderboards 502 for specific previously recorded classes to create a leaderboard 502 that provides the maximum personal performance incentive to the user 106.

Users 106 may also be provided with the ability to deselect the leaderboard 502 entirely and remove it from the user interface 500. In various exemplary embodiments, the exercise machine 102 may incorporate various social networking aspects such as allowing the user 106 to follow other participants, or to create groups or circles of participants. User lists and information may be accessed, sorted, filtered, and used in a wide range of different ways. For example, other users can be sorted, grouped and/or classified based on any characteristic including personal information such as age, gender, weight, or based on performance such as current power output, speed, or a custom score.

The leaderboard 502 may be fully interactive, allowing the user 106 to scroll up and down through the participant rankings, and to select a participant to access their detailed performance data, create a connection such as choosing to follow that participant, or establish direct communication such as through an audio and/or video connection. The leaderboard 502 may also display the user's personal best performance in the same or a comparable class, to allow the user 106 to compare their current performance to their previous personal best. In some examples, such performance information may also be displayed in one or more of the display bars 414, 416. The leaderboard 502 may also highlight certain participants, such as those that the user 106 follows, or provide other visual cues to indicate a connection or provide other information about a particular entry on the leaderboard 502.

In various exemplary embodiments, the leaderboard 502 may also allow the user 106 to view their position and performance information at all times while scrolling through the leaderboard 502. For example, if the user 106 scrolls up toward the top of the leaderboard 502 such as by dragging their fingers upward on the display 104, when the user 106 reaches the bottom of the leaderboard 502, it may lock in position and the rest of the leaderboard 502 will scroll underneath it. Similarly, if the user 106 scrolls down toward the bottom of the leaderboard 502, when the user's window reaches the top of the leaderboard 502, it may lock in position and the rest of the leaderboard 502 will continue to scroll underneath it. In various exemplary embodiments, performance information about other users may also be presented on the leaderboard 502 or in any other format, including formats that can be sorted by relevant performance parameters. Users may elect whether or not to make their performance available to all users, select users, and/or instructors, or to maintain it as private so that no one else can view it.

As shown in FIG. 5, in some examples the leaderboard 502 may provide information 504 indicating the ranking of one or more of the users participating (currently or previously) in the present exercise class. Such a ranking may be, for example, a numerical ranking (e.g., 1-6,936 users, as indicated in the example leaderboard 502 of FIG. 5) indicating the position, ranking, or rating of one or more of the users. Such ranking may be based on output, pace, speed, accuracy, or any of the other performance metrics described herein. In the example shown in FIG. 5, the leaderboard 502 may also include information 506 indicating the actual values associated with the rankings or other information 504. For instance, in the example shown in FIG. 5, the user "Stephanie" may have a ranking of "3," and this ranking for Stephanie may correspond to her output of 2,686 Watts. Similarly, the user "Ashley" may have a ranking of "4," and this ranking for Ashly may correspond to her output of 1,890 Watts. Moreover, in some examples the leaderboard 502 may include information 508 indicating the accuracy with which each of the listed users are following the current instruction provided by the instructor. For instance, in the example shown in FIG. 5, the user "Stephanie" may have an accuracy rating of 13%, and such an accuracy rating may indicate that Stephanie is running at a pace that is 13% above the 6.0 minute mile pace that is currently being requested by the instructor (and as indicated by the executable control 418). Similarly, in the example shown in FIG. 5, the user "Ashley" may have an accuracy rating of 11%, and such an accuracy rating may indicate that Ashley is running at a pace that is 11% above the 6.0 minute mile pace that is currently being requested by the instructor (and as indicated by the executable control 418). While the leaderboard 502 shown in FIG. 5 provides information 504 ranking the various users based on, for example, their respective output (as indicated by the information 506), it is understood that in further examples, the leaderboard 502 may rank the various users based on their respective accuracy rating (as indicated by the information 508), and/or based on any other performance metrics or other information.

Figure 5A:
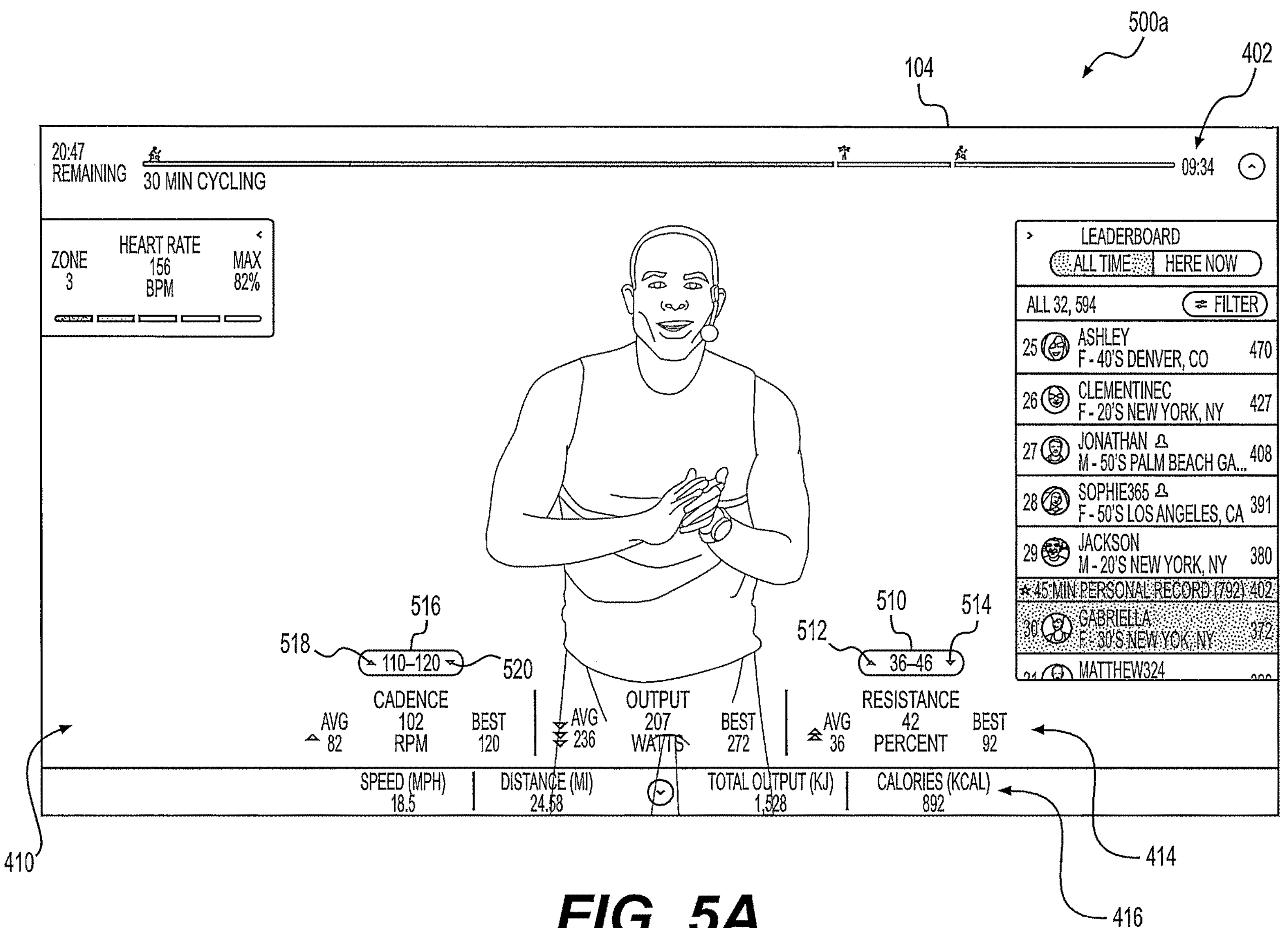
FIG. 5A illustrates yet another user interface of the present disclosure showing video content corresponding to an exercise class, as well as a leaderboard.

FIG. 5A illustrates another example user interface 500*a* of the present disclosure. In such examples, the user interface 500*a* may be substantially similar to the user interface 500 described above with respect to FIG. 5 and/or may be substantially similar to the user interface 200 described above with respect to FIG. 2. As shown in FIG. 5A, such an example user interface 500*a* may include, among other things, a primary window 410 that includes the segmented timeline 402, leaderboard, display bars 414, 416, and/or other items described above with respect to at least FIG. 5. Additionally, the example user interface 500 may include one or more windows 510, 516 overlaid on and/or otherwise displayed together with the primary window 410. In such examples, the windows 510, 516 may include respective executable controls configured to receive inputs, and to direct a corresponding signal to the processor of the digital hardware 148 based at least in part on such inputs. In such embodiments, the processor of the digital hardware 148 may be configured to modify one or more corresponding parameters of the exercise machine 102 based at least in part on the signal and/or the input.

In some embodiments, one or more of the windows 510, 516 may correspond to a respective one of the parameters displayed, indicated, and/or identified by the display bar 414 or the display bar 416. For example, the window 510 may be positioned above, below, near, integral with and/or otherwise in association with the "resistance" information provided in the display bar 414. In such examples, the window 510 may include an executable control 512 configured to receive an input associated with and/or indicative of a desired increase in, for example, a resistance of the belt 120. The window 510 may also include an executable control 514 configured to receive an input associated with and/or indicative of a desired decrease in the resistance of the belt 120. In such examples, the executable controls 512, 514 may be configured to direct respective signals to the processor of the digital hardware 148 based at least in part on such inputs.

Similarly, as shown in FIG. 5A the window 516 may be positioned above, below, near, integral with and/or otherwise in association with the "cadence" information provided in the display bar 414. In such examples, the window 516 may include an executable control 518 configured to receive an input associated with and/or indicative of a desired increase in, for example, a speed or cadence of the belt 120. The window 516 may also include an executable control 520 configured to receive an input associated with and/or indicative of a desired decrease in the speed or cadence of the belt 120. In such examples, the executable controls 518, 520 may be configured to direct respective signals to the processor of the digital hardware 148 based at least in part on such inputs. While example windows 510, 516 and corresponding executable controls 512, 514, 518, 520 have been described with respect to the resistance and cadence information provided by the user interface 500*a*, it is understood that in other examples, the user interface 500*a* may include one or more additional windows and/or executable controls associated with any other information or parameters provided by the user interface 500*a*.

Figure 6:
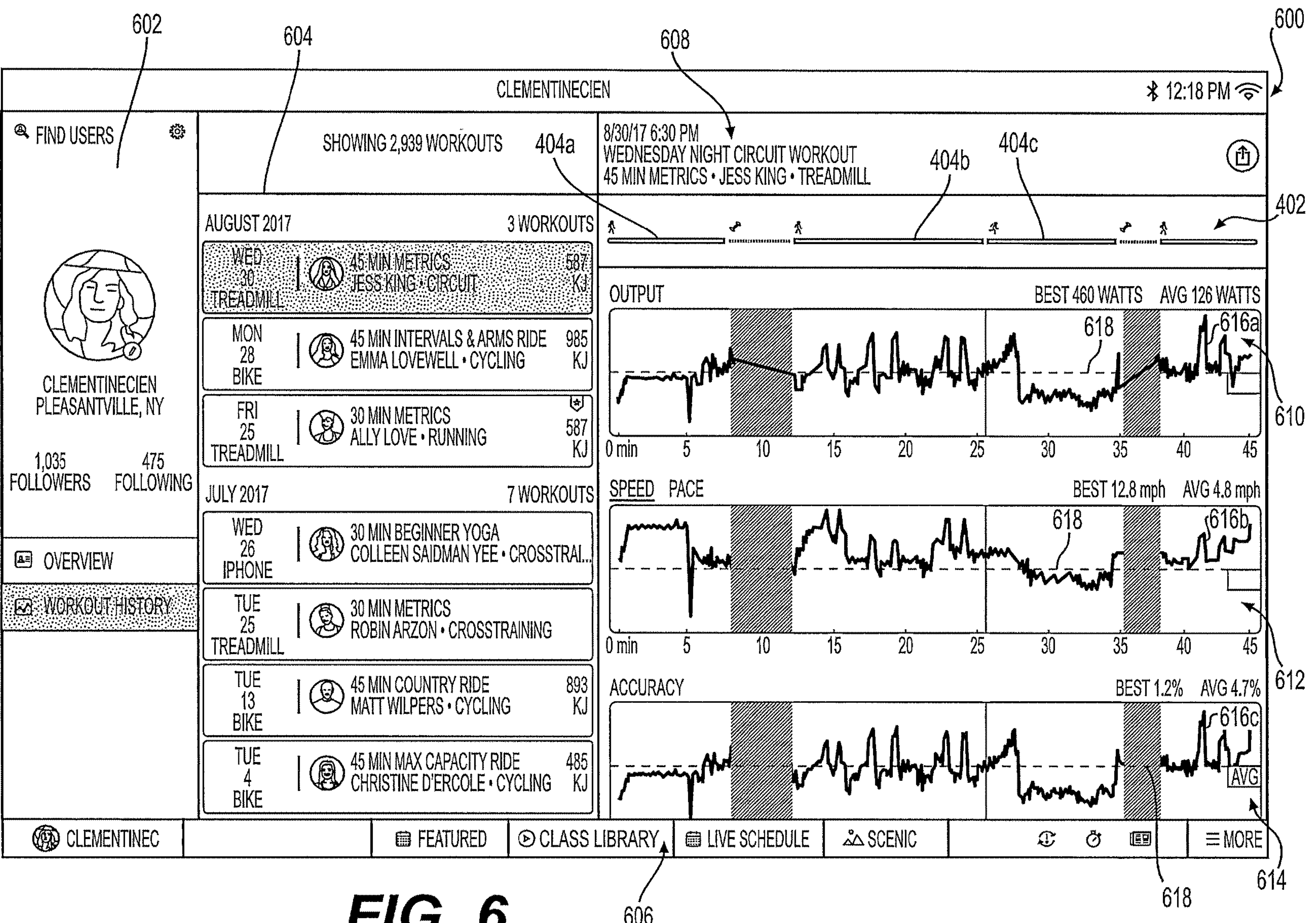
FIG. 6 illustrates still another example user interface of the present disclosure showing a summary of various performance metrics.

FIG. 6 illustrates another example user interface 600 of the present disclosure. In implementations of this disclosure, the user interface 600 may be a workout summary interface. As illustrated, the user interface 600 may include a plurality of sections or windows, including a user identification window 602, a workout window 604, and a workout summary window 606. Although the illustrated interface 600 includes the three windows 602, 604, 606, more or fewer windows may be present in the interface.

The user identification window 602 may include information about the user. Such information may include, among other things, an identification of the user 106, e.g., a picture, name, avatar, or the like, a number of followers the user 106 has, a number of fellow participants that the user 106 is following, the total lifetime runs, rides, circuits, or other workouts in which the user 106 has completed and/or been a participant, an identification of achievements or rewards the user has earned, records or goals, a timeline of the user's recent workout activity, and/or other such general information associated with the user 106 and/or the user's workout activities. In further examples, the information provided in the user identification window 302 may be provided in alternative formats, windows, or locations.

The workout window 604 may include information about workouts, including available classes and/or classes already completed by the user 106. In some implementations, the workout window 604 may list upcoming live classes or available, pre-recorded on-demand classes. The workout window 604 may also include associated filters and/or search tools allowing the user 106 to customize the information contained in the workout window 604. In the illustrated embodiment, the workout window 604 includes a listing of workouts or other exercise classes performed by the user 106. The workouts are illustrated as arranged in a chronological list, although the workouts may be otherwise represented. Moreover, the workout window 604 may further include one or more of a score achieved by the user 106 during each exercise class (e.g., an output score), the date and/or time of the class, an identification of the instructor, and/or other information. The user interface 600 may also include one or more additional windows and/or other formats useful in providing additional information regarding the workout history of the user 106.

The workout summary window 606 may provide information about a specific workout, including performance metrics indicative of the user's performance for the specific workout. For instance, the workout summary window 606 may include information about a completed workout selected in the workout window 604. The workout summary window 606 may include workout information 608 indicative of the workout detailed in the workout summary window 606. By way of non-limiting example, the workout information 608 may include one or more of a date, time, duration, workout name, instructor name, workout type (e.g., cycling, walking/running, combined workout, circuit workout, etc.) targeted muscle group(s) for the workout, and/or other information.

In some examples, the workout summary window 606 may also include at least part of the segmented timeline 402 described above with respect to FIG. 4. For instance, in the example user interface 600 illustrated in FIG. 6 the summary window 606 may correspond to a treadmill-based circuit workout, and the illustrated segmented timeline 402 may include one or more segments 404*a*, 404*b*, 404*c* . . . 404*n* (collectively, "segments 404") corresponding to respective portions, parts, or other segments of an exercise class. The segmented timeline 402 may also include visual indicia indicating an activity requirement (e.g., run, jog, sprint, lift weights, etc.), an equipment requirement (e.g., dumbbells, yoga mat, etc.) and/or other requirement associated with a respective segment of the exercise class. Together, the segments 404 and corresponding visual indicia of the segmented timeline 402 may provide a graphical representation of the entire workout.

The workout summary window 606 may also include one or more workout summary graphics 610, 612, 614 illustrated in association with the segments 404 of the segmented timeline 402. For example, as shown in FIG. 6 a first workout summary graphic 610 shows an output (e.g., a measure of performance, which may be a combination of one or more factors normalized across participants) for the user 106 over the duration of the workout, the second workout summary graphic 612 shows a speed for the user 106 over the duration of the workout, and the third workout summary graphic 614 the accuracy with which the user 106 followed various instructor commands over the duration of the workout. As illustrated, the workout summary graphics 610, 612, 614 may be rendered as graphs including respective plot lines 616*a*, 616*b*, 616*c* (collectively, "plot lines 616") indicating user performance throughout the workout. The respective plot lines 616 may represent sensor information received from sensors associated with exercise equipment (e.g., the exercise machine 102, body-worn sensors, etc.) used by the user 106. For instance, speedometers, pedometers, accelerometers, position sensors, gyroscopes, biometric sensors, or the like, associated with the exercise machine 102 and/or with one or more wearable devices, may sense information associated with the exercise equipment and/or the user 106, and such information may be used to create the respective plot lines 616.

The workout summary graphics 610, 612, 614 may also include respective axes 618 representing an average value for the specific metric. In the illustrated implementations, the axes 618 represent a user-specific average (e.g., an average specific to the user 106) of the respective metrics, as determined based on the entire workout. However, in other embodiments, the axes 618 may indicate an average for all participants of the workout, e.g., so the user 106 can see her performance relative to other participants. In other implementations, the axes 618 may not be representative of an average, but may instead be a predetermined reference value, which may include a target value or a value associated with a previous undertaking of the workout.

In further examples, graphics other than the workout summary graphics 610, 612, 614 may also or alternatively be provided in the workout summary window 606. For example, as illustrated in the graphic 612, the user 106 may be able to select a "pace" graphic instead of the illustrated "speed" graphic. For example, such a pace graphic may show a minute-per-mile plot as opposed to the illustrated mile-per-hour. Moreover, the displayed and/or available workout summary graphics may vary based on the workout type and/or available information. For instance, workout summary graphics associated with weight-based segments of a workout may be rendered based on information from user-worn sensors or sensors disposed on weights used to perform those segments of the workout. Moreover, sensors on other types of equipment may also be used. By way of non-limiting example, a workout may include segments executed on a cycle, such as a stationary cycle. In such examples, sensors associated with the cycle may be used to render the workout summary graphics. Other modifications and alternatives may also be appreciated by those having ordinary skill in the art, with the benefit of this disclosure.

Figure 6A:
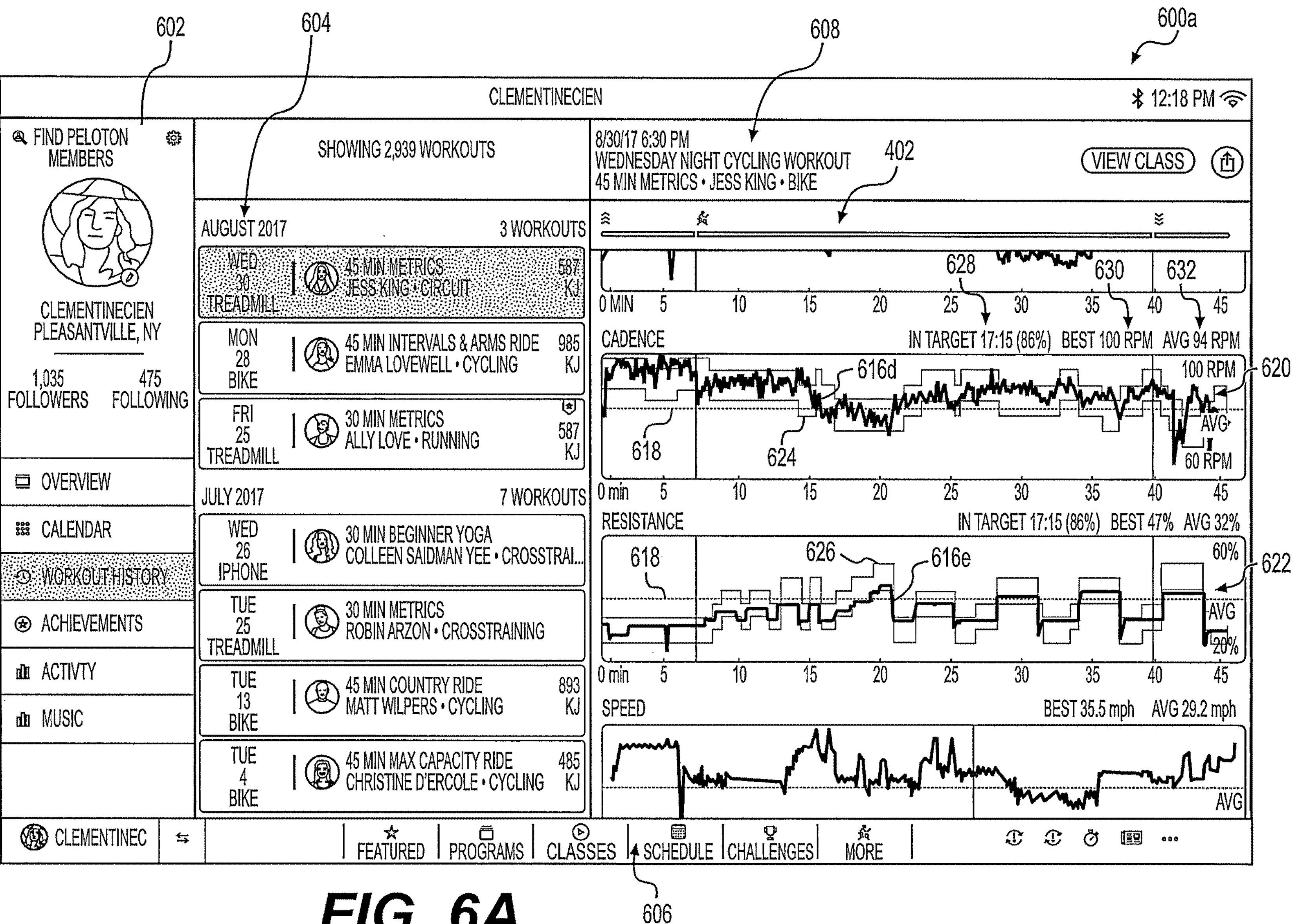
FIG. 6A illustrates a further example user interface of the present disclosure showing a summary of various performance metrics.

FIG. 6A illustrates another example user interface 600*a* of the present disclosure. In such examples, the user interface 600*a* may be substantially similar to the user interface 600 described above with respect to FIG. 6. For instance, the user interface 600*a* may include, among other things, a user identification window 602, a workout window 604, a workout summary window 606, workout information 608, a segmented timeline 402, and/or other components described above with respect to FIG. 6.

As shown in FIG. 6*a*, in some examples the workout summary window 606 may include one or more workout summary graphics 620, 622 illustrated in association with the segments 404 of the segmented timeline 402. For example, a workout summary graphic 620 may be indicative of a cadence of the user 106 (e.g., a cadence of the belt 120) over the duration of the workout, and an additional workout summary graphic 622 may be indicative of a resistance of the belt 120 over the duration of the workout. As illustrated, the workout summary graphics 620, 622 may be rendered as graphs including respective plot lines 616*d*, 616*e* indicating user performance throughout the workout. As described above with respect to FIG. 6, the respective plot lines 616*d*, 616*e* may represent sensor information received from sensors associated with exercise equipment (e.g., the exercise machine 102, body-worn sensors, etc.) used by the user 106, and in such examples, such information may be used to create the respective plot lines 616*d*, 616*e*.

As described with respect to FIG. 6, the workout summary graphics 620, 622 may include respective axes 618 representing an average value for the specific metric. In the illustrated implementations, the axes 618 represent a user-specific average (e.g., an average specific to the user 106) of the respective metrics, as determined based on the entire workout. However, in other embodiments, the axes 618 may indicate an average for all participants of the workout, or may be a predetermined reference value (e.g., a target value).

In the example user interface 600*a* of FIG. 6A, the workout summary graphics 620, 622 may also include respective visual indicia 624, 626 indicating average ranges associated with the respective metrics. For example, the visual indicia 624 may comprise a series of bars, boxes, line segments, shaded/hatched/colored areas, or other objects indicating an average cadence range associated with a corresponding segment of the workout. Likewise, the visual indicia 626 may comprise a series of bars, boxes, line segments, shaded/hatched/colored areas, or other objects indicating an average resistance range associated with a corresponding segment of the workout. Similar to the axes 618, the visual indicia 624, 626 may comprise user-specific average ranges, average ranges determined based on all participants of the workout, predetermined reference ranges (e.g., target ranges), and/or other ranges of values corresponding to the particular workout identified by the workout information 608. In any of the examples described herein, one or more of the workout summary graphics 620, 622 of the user interface 600*a* may also include information 628 indicating an amount of time, a percentage of the workout, and/or other indicia representing the user's adherence to, for example, a target range (e.g., a target cadence range) indicated by the visual indicia 624. One or more of the workout summary graphics 620, 622 may also include information 630 indicating a user-specific best value (e.g., a best cadence, belt speed, etc.) for the workout corresponding to the parameter associated with the respective workout summary graphic 620, 622. One or more of the workout summary graphics 620, 622 may further include information 632 indicating a user-specific average value (e.g., an average cadence, average belt speed, etc.) for the workout corresponding to the parameter associated with the respective workout summary graphic 620, 622.

Figure 7:
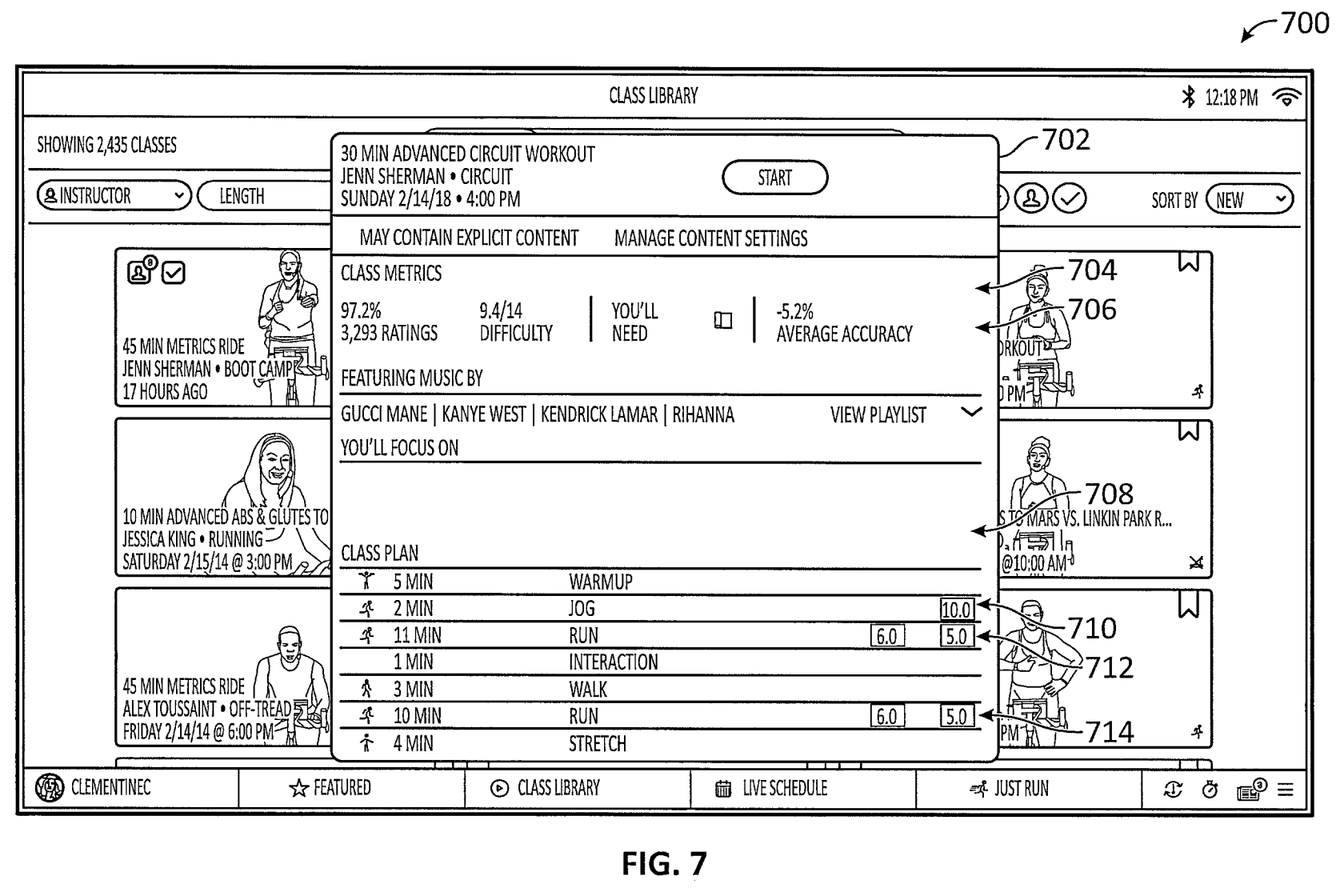

FIG. 7 illustrates still another example user interface 700 of the present disclosure. Such an example user interface 700 may include a window 702 showing a variety of pre-workout information 704 that may be useful to a user 106 when selecting a particular workout. For example, such information 704 may assist the user 106 in comparing a particular workout to various other available workouts so that the user 106 may select a workout based on difficulty level, activities included in the workout (e.g., workout content), and/or other criteria. As shown in FIG. 7, such information 704 may include a plurality of metrics 706 associated with the particular exercise class. Such metrics 706 may include, among other things, a difficulty ranking, an indication of various exercise equipment needed to participate in the class (e.g., an icon, image, text, or other indicia of a dumbbell, a yoga mat, etc.) an average rating, an average accuracy, and/or other metrics associated with (e.g., descriptive of) the exercise class. In some examples, such information 704 may also include an indication (e.g., an icon, image, text, or other indicia) of various muscle groups or other areas (e.g., arms, legs, cardio, abs, core, etc.) that the exercise class will focus on.

Additionally or alternatively, the information 704 may include a class plan 708 providing a breakdown of the different activities (e.g., jog, run, walk stretch, lift, etc.) included in the exercise class, a length of time associated with each respective activity, an icon, image, symbol, or other visual indicia associated with each activity, etc. In some examples, such a class plan 708 may also include a listing, summary, or other indication of the respective executable controls included in the exercise class and corresponding to the different segments of the exercise class. For example, the exercise class corresponding to the example class plan 708 may have an 11-minute run segment that includes a "6.0" minute mile pace executable control 418. The exercise class corresponding to the example class plan 708 may also have a 10-minute run segment that includes a "6.0" minute mile pace executable control 418. It is understood that such executable controls may be generated based at least in part on respective performance commands uttered by an instructor during the exercise class and/or based at least in part on user data including respective settings (associated with a common performance metric) used on a plurality of exercise machines during playback of the exercise class. In some examples, such a class plan 708 may further include one or more indications 710, 712, 714 of an accuracy metric associated with segments of the exercise class. For example, the indication 712 may indicate that, on average, previous users participating in the exercise class corresponding to the class plan 708 achieved an accuracy rating/metric of 5.0% when the "6.0" minute mile pace executable control 418 was provided (e.g., during the 11-minute run segment). Similarly, the indication 714 may indicate that, on average, previous users participating in the exercise class achieved an accuracy rating/metric of 5.0% when the "6.0" minute mile pace executable control 418 was provided during the 10-minute run segment. A user 106 considering participating in the exercise class may find the information 704 included in the window 702 useful in determining whether the particular exercise class is appropriate for her. Such information may also be useful in evaluating the difficulty and/or accuracy of the various executable controls 418 provided during the exercise class.

FIG. 7A illustrates yet another example user interface 700*a* of the present disclosure. The user interface 700*a* may be substantially similar to the user interface 700 described above with respect to FIG. 7, and may include one or more substantially similar components. For instance, the example user interface 700*a* may include a window 702*a* showing a variety of pre-workout information 704 that may be useful to a user 106 when selecting a particular workout. As shown in FIG. 7*a*, such information 704 may include a plurality of metrics 706 associated with the particular exercise class. Such metrics 706 may include, among other things, a difficulty ranking, an indication of various exercise equipment needed to participate in the class (e.g., an icon, image, text, or other indicia of a dumbbell, a yoga mat, etc.) an average rating, an average accuracy, and/or other metrics associated with (e.g., descriptive of) the exercise class. Additionally or alternatively, the information 704 may include a class plan 708 providing a breakdown of the different activities (e.g., jog, run, walk stretch, lift, etc.) included in the exercise class, a length of time associated with each respective activity, an icon, image, symbol, or other visual indicia associated with each activity, etc. In some examples, the class plan 708 may include an indication (e.g., an icon, image, text, or other indicia) of various muscle groups or other areas (e.g., arms, legs, cardio, abs, core, etc.) that the exercise class will focus on.

As shown in FIG. 7A, the information 704 may also include one or more target metrics 716 associated with the exercise class. For instance, such target metrics 716 may include a target cadence plot, a target cadence range, an average cadence/belt speed, and/or other target cadence information 718 corresponding to the exercise class. Such target metrics 716 may also include a target resistance plot, a target resistance range, an average resistance value, and/or other target resistance information 720 corresponding to the exercise class. It is understood that the target cadence information 718 may correspond to one or more of the visual indicia 624 described above with respect to FIG. 6A. Likewise, the target resistance information 720 may correspond to one or more of the visual indicia 626 described above with respect to FIG. 6A. In some examples the information 704 provided by the window 702*a* may further include an indication 722 of the number of members or other users 106 currently working out and/or otherwise participating in the exercise class corresponding to the information 704.

Figure 7B:
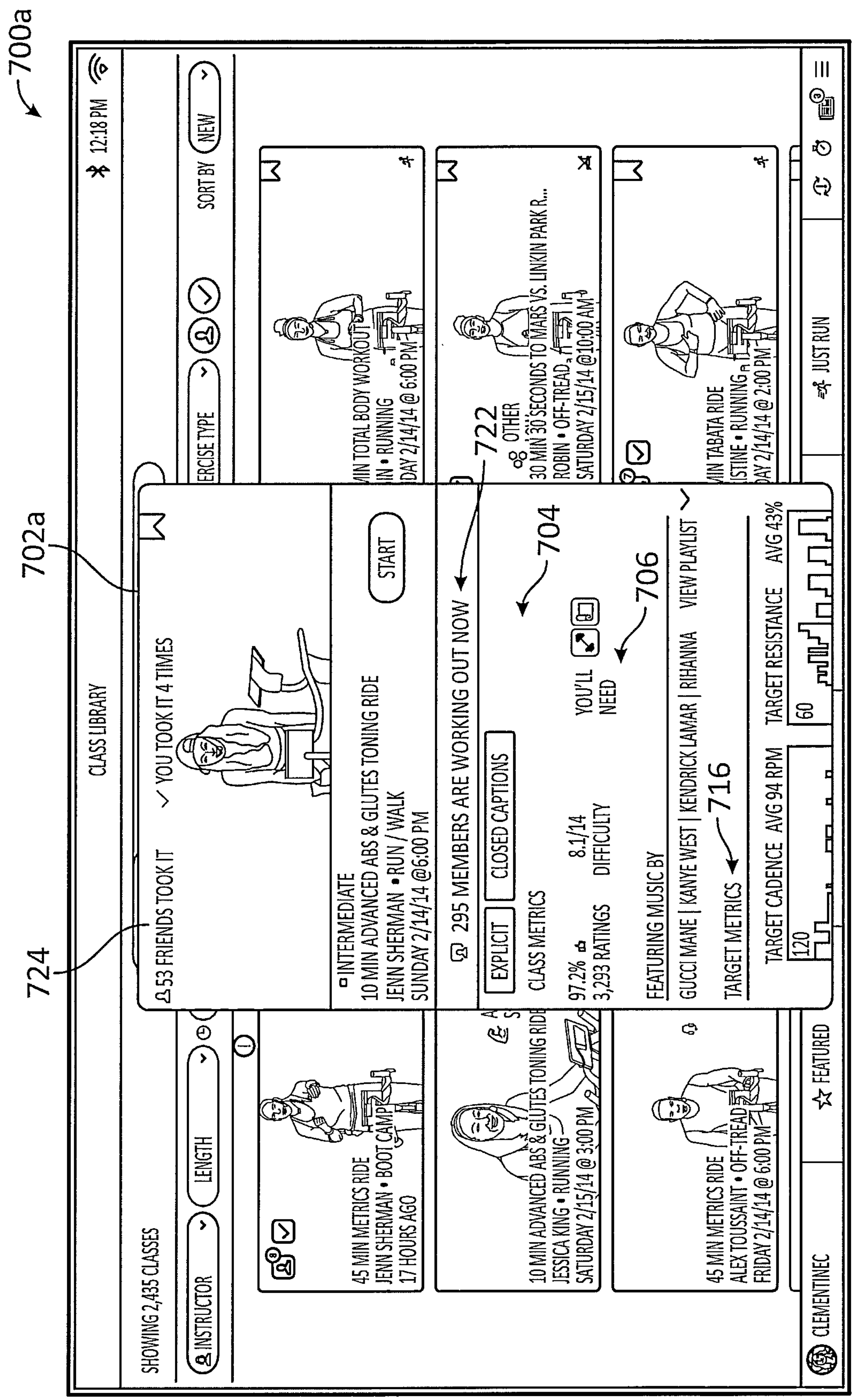
FIG. 7B illustrates portions of the example user interface shown in FIG. 7A.

FIG. 7B illustrates portions of the user interface 700*a* in further detail. For instance, as shown in FIG. 7B, the user interface 700*a* may comprise a window 702 providing the pre-workout information 704, metrics 706, target metrics, and/or indication 722 of the number of members or other users 106 currently participating in the exercise class, as described above with respect to FIG. 7A. Additionally, as shown in FIG. 7B, the user interface 700*a* may provide an indication 724 of the number of friends (e.g., linked/stored/affiliated friends of the user 106) that have taken the particular exercise class in the past. Such an indication 724 may also indicate whether the particular user 106 has taken the exercise class in the past and/or a number of times the user 106 has taken the exercise class.

Figure 8:
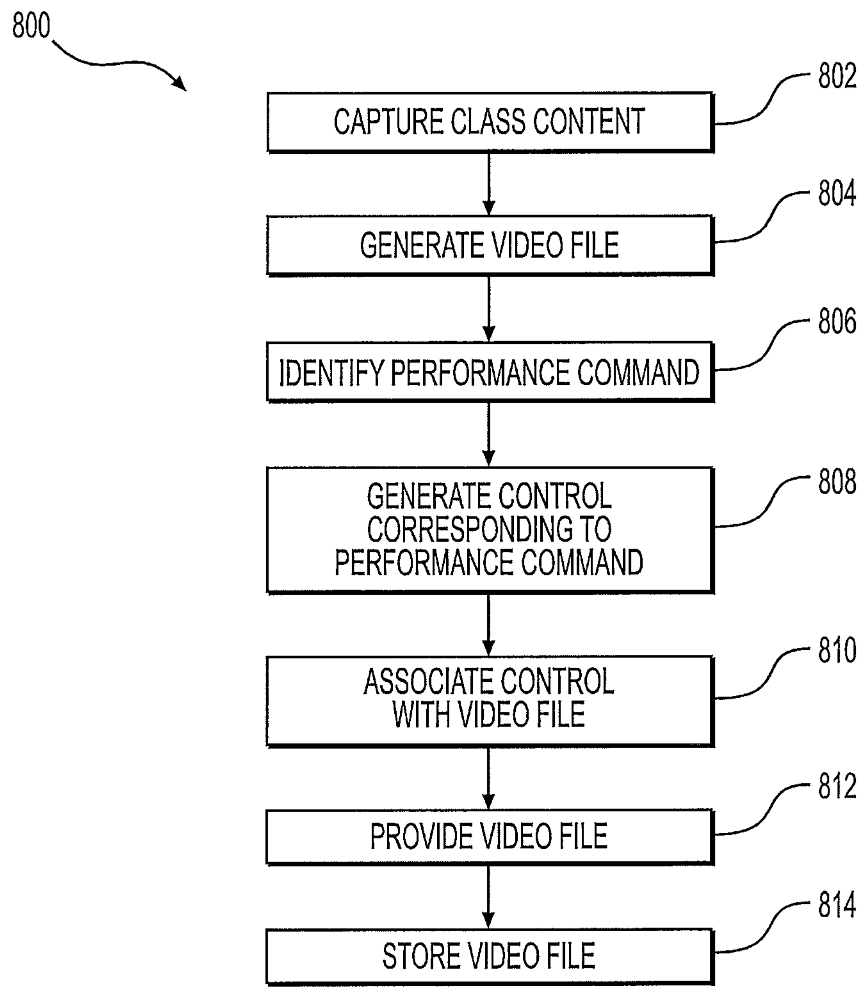
FIG. 8 illustrates a flowchart indicative of an example method of the present disclosure.

FIG. 8 illustrates a flow chart depicting another example method 800 of the present disclosure. The example method 800 is illustrated as a collection of steps in a logical flow diagram, which represents operations that can be implemented in hardware, software, or a combination thereof. In the context of software, the steps represent computer-executable instructions stored in memory. When such instructions are executed by, for example, the processor of the digital hardware 148 and/or by one or more processors of the server 302 described above, such instructions may cause the processor of the digital hardware 148 and/or the one or more processors of the server 302 to perform the recited operations. The order in which the operations are described is not intended to be construed as a limitation, and any number of the described steps can be combined in any order and/or in parallel to implement the process. Additionally, the method 800 may include any of the operations described herein with respect to additional and/or other methods of the present disclosure, and vice versa. For discussion purposes, and unless otherwise specified, the method 800 is described with reference to the networked exercise system 300, an instructor using a first exercise machine 102 to perform an exercise class in a studio or other location comprising one or more of the video cameras 308, microphones 310, and/or other components of the networked exercise system 300, a user 106 using a second exercise machine 102, one or more user interfaces 200, 400, 500, 600, 700, and/or other items shown in FIGS. 1-7. In particular, although any part of and/or the entire method 800 may be performed by the processor of the digital hardware 148, unless otherwise specified, the method 800 will be described below with respect to the one or more processors of the server 302, and/or other components of the networked exercise system 300 for ease of description.

With reference to FIG. 8, at 802 the server 302 and/or other components of the networked exercise system 300 may capture content associated with an exercise class being performed by an instructor. In such examples, the instructor may be utilizing a first exercise machine 102 to perform the exercise class in a studio, gym, and/or other workout facility. In such examples, one or more video cameras 308, microphones 310, music players 312, audio mixers 314, and/or other components of the networked exercise system 300 may be utilized by and/or in conjunction with the server 302 to sense, record, and/or otherwise capture the exercise class content at 802. For example, at 802 the server 302 may capture audio content corresponding to the exercise class being performed by the instructor, as well as video content corresponding to the exercise class.

At 804, the server 302 may generate a video file comprising the audio content, the video content, and/or any other content captured at 802. For example, audio content may be captured at 802 in an audio track, and video content may be captured at 802 in a video track separate from the audio track. In such examples, at 804 the analog to digital converter 316, the video encoder 320, the video transcoder 324, and/or other components of the server 302 may merge the audio track and the video track to form a single digital video file at 804. Additionally or alternatively, the audio content and the video content may be captured at 802 utilizing at least one analog device. In such examples, at 804, the analog to digital converter 316 and/or other components of the server 302 may convert any such analog content to digital content, and may generate a digital video file at 804 comprising digital audio content and digital video content. In still further examples, at 802, the audio content and the video content may be captured in digital form and in a single content capture (e.g., digital recording) process. In such examples, a video file (e.g., a digital video file) may be generated at 802 upon and/or as part of capturing the audio content and video content.

At 806, the server 302 may identify one or more performance commands (e.g., a performance command included in the audio content captured at 802) uttered by the instructor during the exercise class. For example, natural language processing software and/or other voice recognition software operating on the server 302 may identify a verbal command uttered by the instructor during the exercise class, and/or after the exercise class has been completed. In such examples, at 806 the natural language processing software and/or other voice recognition software may provide an indication of the verbal command to the video encoder 320, and/or other components of the server 302 operable to generate an executable command. In some examples, the natural language processing software and/or other voice recognition software may additionally or alternatively provide the indication of the verbal command to one or more operators of the server 302 (e.g., via a display or other output device operably connected to the server 302), and such operators may confirm, for example, the accuracy of the identified verbal command and/or the placement of a corresponding executable control within the video file generated at 804. In still further examples, at 806 the performance command may be identified and/or recognized by an operator viewing the exercise class (in real time and/or upon playback of the exercise class) without the use of natural language processing software and/or other voice recognition software.

As noted above, in some embodiments the instructor may utter a relatively specific performance command during an exercise class. Examples of such relatively specific performance commands may include, "run at a 6.0 minute mile pace," "go to a 5.0 incline," "reach your Zone 4 power output for the next 2 minutes," or any other relatively definite command corresponding to a desired speed of the belt 120, a desired running speed of the user 106, a desired incline of the deck 112, a desired power zone of the user 106, a desired output level of the user 106, a desired braking force or resistance of the exercise machine 102, a position of a seat associated with the exercise machine 102, a stride type, a pedal cadence of the user 106, and/or any other such parameter. In such examples, at 806 the server 302, an operator of the server 302, and/or any other operator of a control station associated with the location (e.g., a studio) in which the instructor is performing the exercise class, may identify the verbal command uttered by the instructor. In some examples, at 806 natural language processing software and/or other voice recognition software operating on the server 302 may provide an indication of the verbal command to the video encoder 320, and/or other components of the server 302 operable to generate an executable command. Additionally, at 806 the server 302 may identify a timestamp associated with the command (e.g., an elapsed time in the video file generated at 804). Such a timestamp may identify the time during the exercise class at which the instructor uttered the command.

In additional embodiments, the instructor may utter a relatively abstract or vague command during an exercise class. Examples of such relatively abstract or vague commands may include, "jog for a few minutes," "let's go up this hill," or any other command that may have a different meaning for respective users 106 participating in the exercise class, but that may still correspond to the current exercise segment and/or current part of the exercise class being performed by the instructor. In such examples, at 806 the server 302, an operator of the server 302, and/or an operator of a control station associated with the location (e.g., an exercise studio) in which the instructor is performing the exercise class, may identify the relatively abstract verbal command uttered by the instructor. In some examples, at 806 natural language processing software and/or other voice recognition software operating on the server 302 may provide an indication of the verbal command to the video encoder 320, and/or other components of the server 302 operable to generate an executable command. Additionally, at 806 the server 302 may identify a timestamp associated with the relatively abstract command.

At 808, the server 302 may generate an executable control 418 corresponding to the exercise class being performed by the instructor. As noted above, in some examples, one or more executable controls 418 generated at 808 may be operable to modify a parameter of an exercise machine 102 (e.g., a second exercise machine 102 used by a user 106 to participate in the exercise class). For example, at 808 the server 302 may generate an executable control 418 corresponding to the performance command identified at 806. One or more executable controls 418 generated at 808 may comprise data files, text files, digital files, metadata, instructions, and/or any other electronic file executable by the processor of the digital hardware 148. When an example executable control 418 generated at 808 is executed by the processor of the digital hardware 148, the processor may cause display of the text or other information associated with the executable control 418 via a user interface (e.g., user interface 400). In some examples, such text (e.g., guidance, an encouraging statement, etc.) may be displayed via one or more respective windows 422 included in the user interface 400. In some examples, such windows 422, executable controls 418, and/or other portions of the example user interfaces 400 described herein may be provided to the user 106 during an exercise class as a means of communicating with, guiding, and/or encouraging the user 106. In some examples, such windows 422 and/or executable controls 418 may not be configured to receive user input and may not be operable to modify on or more parameters of the exercise machine 102. In additional examples, on the other hand, one or more of the executable controls 418 described herein may be configured to receive a touch input from the user 106 via the display 104. In such examples, the one or more of the executable controls 418 may be configured to modify at least one parameter of the second exercise machine 102 (e.g., the exercise machine 102 that the user 106 is utilizing to participate in the exercise class), based at least in part on such an input. In example embodiments of the present disclosure, one or more of the executable controls 418 generated at 808 may comprise one or more settings associated with modifying a parameter of the second exercise machine 102.

For example, in embodiments in which the command identified at 806 comprises a relatively specific command, the server 302 may configure the executable control 418 such that, when the executable control 418 is processed and/or executed by the processor of the digital hardware 148 (e.g., of the second exercise machine 102), the processor of the digital hardware 148 may cause a component of the exercise machine 102 (e.g., a motor of the deck 112 controlling the speed of the belt 120) to operate and/or perform an action specifically defined by the executable control 418. For example, in embodiments in which an example relatively specific command identified at 806 comprises "run at a 6.0 minute mile pace," at 808 the server 302 may generate a corresponding executable control 418 that includes instructions, metadata, and/or other information or components which, when executed by the processor of the digital hardware 148, will cause the motor of the deck 112 controlling the speed of the belt 120 to drive the belt 120 to rotate at a belt speed corresponding to a 6.0 minute mile pace. Similar instructions may be included in an executable control 418 directed to a particular power zone, a particular incline of the deck 112, a particular pedal cadence, a particular stationary bicycle braking resistance, and/or any other parameter of the exercise machine 102.

On the other hand, in embodiments in which the command identified at 806 comprises a relatively vague or abstract command, the server 302 may configure the executable control 418 such that, when the executable control 418 is processed and/or executed by the processor of the digital hardware 148 (e.g., of the second exercise machine 102), the processor of the digital hardware 148 may determine an appropriate (e.g., a best fit) response corresponding to the executable control 418 before causing one or more components of the exercise machine 102 to operate in a modified manner. For example, in embodiments in which an example relatively abstract command identified at 806 comprises "jog for a few minutes," at 808 the server 302 may generate an executable control 418 including instructions, metadata, and/or other information which when executed by a processor of an exercise machine 102 (e.g., a second exercise machine 102) may cause the belt 120 of such an exercise machine 102 to rotate at a 4.0 minute mile pace, and/or at any other relatively common jogging pace, and such a setting of the executable control 418 may comprise a default setting. Such a default setting may be associated with the executable control 418 at 808 in situations in which relatively little user data is available corresponding to the particular user 106, a user profile of the user 106 does not include user data associated with a setting or preference of the user 106 related to the abstract command identified at 806, and/or in any other situation in which the server 302 does not have access to adequate information corresponding to the user 106. Alternatively, in examples in which a user profile of the user 106 identifies a preferred jogging pace, and/or in which the database 304 includes stored user data or other information indicating previously selected, previously customized, and/or previously entered jogging speeds of the particular user 106, a weight, height, age, gender, or other physical characteristics of the user 106, and/or other such information, at 808 the server 302 may generate an executable control 418 configured to cause the belt 120 to rotate at a jogging pace that corresponds to such user-specific information.

In any of the examples described herein in which a relatively vague or abstract command has been identified, the server 302 may generate an executable control 418 at 808 corresponding to such a command, and upon receiving a touch input via the executable control 418 while the exercise class is being presented to the user 106 via the user interface 500, the processor of the digital hardware 148 may determine an appropriate response (e.g., an appropriate modification of one or more parameters of the exercise machine 102) based on user data stored within a memory of the digital hardware 148 and/or stored within the database 304 associated with the server 302. As noted above, such an appropriate response, may comprise a default setting (e.g., a default jogging speed, and/or a default deck incline associated with jogging), a previously selected, previously customized, and/or previously entered setting (e.g., a jogging speed and/or a jogging deck incline included in the user profile of the user 106), and/or a setting that is determined by the processor of the digital hardware 148 and/or by the processor of the server 302 based at least in part on user data (e.g., aggregate user data corresponding to the user 106 participating in one or more previous exercise classes using the exercise machine 102) stored within a memory of the digital hardware 148 and/or stored within the database 304.

At 810 the server 302 may embed, link, and/or otherwise associate the executable control 418 with the video file generated at 804 such that playback of at least part of the video file by the processor of the digital hardware 148 (e.g., by the processor of the second exercise machine 102) via the display 104 may result in display of the executable control 418. In particular, at 810 the server 302 may link the executable control 418 to a part of the video file corresponding to the timestamp associated with the command and identified at 806. In such examples, the timestamp may comprise an elapsed time of the video file generated at 804 and/or during the exercise class at which the instructor uttered the command. As a result, when providing the exercise class to the user 106 via the user interface 500 (e.g., either in substantially real time via live streaming, and/or upon playback of the exercise class using an archived video file), the processor of the digital hardware 148 (e.g., the processor of the second exercise machine 102) may provide the executable control 418 at the point in time during the exercise class in which the instructor uttered the verbal command.

At 812, the server 302 may provide the executable control 418, together with the video file generated at 804, to the processor of the digital hardware 148. In such examples, the video packetizer 326 of the server 302 may provide one or more signals to the exercise machine 102 (e.g., the second exercise machine 102) via the network 306, and such signals may include, at least part of the video file and/or the executable control 418 embedded therein. In some examples, such as an example in which a user 106 is live streaming the exercise class in substantially real-time, the server 302 may provide the video file generated at 804 and the executable control 418 generated at 808, via the network 306, as part of a live stream of the exercise class. Alternatively, in examples in which the user 106 is participating in an archived exercise class, at 812, the server 302 may provide the video file generated at 804 and the executable control 418 generated at 808, via the network 306, as part of a transmission of the archived exercise class.

Figure 9:
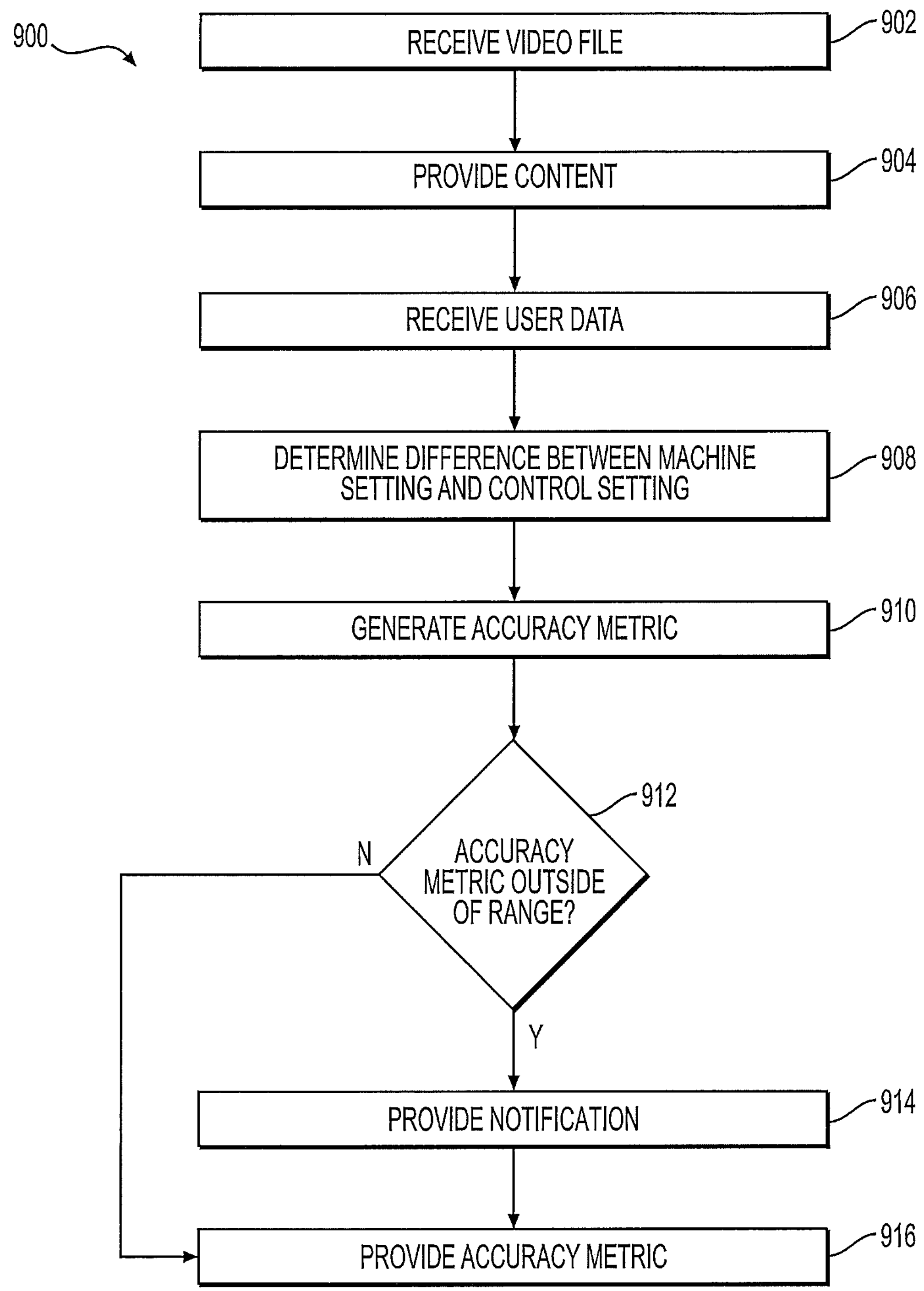
FIG. 9 illustrates a flowchart indicative of another example method of the present disclosure.

Further, at 814, the server 302 may save and/or otherwise store the executable control 418 generated at 808 together with the video file generated at 804. In such examples, the executable control 418 may be linked to, embedded within, associated with, and/or otherwise stored with the video file such that, upon playback of the video file, the executable control 418 may be displayed as part of a user interface 500 presented to the user 106 via the display 104. Further, while the previous disclosure indicates that the server 302 may perform one or more operations of the method 800, in any of the examples described herein, any of the operations described above with respect to the method 800 may be performed, in whole or in part, by the server 302, an operator of the server 302, an operator of a control station at which an exercise class is being performed by an instructor, and/or by any combination thereof FIG. 9 illustrates a flow chart depicting another example method 900 of the present disclosure. Similar to the method 800 described above, the example method 900 is illustrated as a collection of steps in a logical flow diagram, which represents operations that can be implemented in hardware, software, or a combination thereof In the context of software, the steps represent computer-executable instructions stored in memory. When such instructions are executed by, for example, the processor of the digital hardware 148 and/or by one or more processors of the server 302 described above, such instructions may cause the processor of the digital hardware 148 and/or the one or more processors of the server 302 to perform the recited operations. Such computer-executable instructions may include routines, programs, objects, components, data structures, and the like that perform particular functions or implement particular abstract data types. The order in which the operations are described is not intended to be construed as a limitation, and any number of the described steps can be combined in any order and/or in parallel to implement the process. For discussion purposes, and unless otherwise specified, the method 900 is described with reference to the local system 100, the exercise machine 102, the user 106, the user interfaces 200, 400, 500, 600, 700, and/or other items shown in FIGS. 1-7. In particular, although any part of and/or the entire method 900 may be performed by the one or more processors of the server 302, and/or other components of the networked exercise system 300, unless otherwise specified, the method 900 will be described below with respect to the processor of the digital hardware 148 for ease of description.

With reference to FIG. 9, at 902 the processor of the digital hardware 148 may receive, at an exercise machine 102 and via the content distribution network 306 described above, a video file including content associated with an exercise class. For example, such a video file may include audio content and video content associated with an instructor performing an exercise class via an additional (e.g., a remote) exercise machine 102. In such examples, the instructor may be utilizing an exercise machine 102 to perform the exercise class in a studio, gym, and/or other workout facility. In such examples, one or more video cameras 308, microphones 310, music players 312, audio mixers 314, and/or other components of the networked exercise system 300 may be utilized by and/or in conjunction with the server 302 of the networked exercise system 300 described above to sense, record, and/or otherwise capture the exercise class content included in the received video file. Additionally, as noted above with respect to at least the method 800 of FIG. 8, the video file may include, among other things, one or more executable controls. Further, in some examples the processor of the digital hardware 148 may receive the video file at 902 via a live stream of the exercise class. In such examples, the instructor may perform the exercise class in the workout facility described above, and the processor of the digital hardware 148 may receive the video file at 902 substantially simultaneously (e.g., in substantially real-time). Alternatively, the video file received at 902 may comprise a stored recording of an exercise class previously performed by the instructor, and in such examples, the processor of the digital hardware 148 may receive the video file at 902 at a later time and/or date.

At 904, the processor of the digital hardware 148 may provide the content included in the video file via a display 104 associated with the exercise machine 102 being utilized by a user 106 wishing to participate and/or participating in the exercise class. For example, as noted above, one or more displays 104 may be mounted directly to the exercise machine 102 or otherwise placed within view of a user 106. In various exemplary embodiments, the one or more displays 104 allow the user 106 to view content relating to a selected exercise class both while working out on the exercise machine 102 and while working out in one or more locations near or adjacent to the exercise machine 102. The display 104 may comprise a touch screen, a touch-sensitive (e.g., capacitance-sensitive) display, and/or any other device configured to display content and receive input (e.g., a touch input, tap input, swipe input, etc.) from the user 106.

Accordingly, providing the content at 904 may include playing back (e.g., displaying) the exercise class via the display 104 and/or via one or more speakers associated with the display 104 or the exercise machine 102. Providing the content at 904 may also include displaying one or more executable controls 418 included in the video file, via the display 104, during a particular part of the video file. For example, as noted above with respect to the method 800, the server 302 may generate an executable control 418 corresponding to the exercise class being performed by the instructor. For example, the server 302 may generate an executable control 418 corresponding to a performance command uttered by the instructor as the instructor performs the exercise class. Alternatively, the server may generate an executable control 418 based at least partly on user data received from a plurality of exercise machines and associated with a common performance metric. Such executable controls 418 may be embedded within and/or otherwise associated with the video file received at 902. When such an executable control 418 is executed by the processor of the digital hardware 148 at 904, the processor of the digital hardware 148 may cause display of the text or other information associated with the executable control 418 via a user interface (e.g., user interface 400). In some examples, such text (e.g., guidance, an encouraging statement, etc.) may be displayed via one or more respective windows 422 included in the user interface 400. In some examples, such windows 422, executable controls 418, and/or other portions of the example user interfaces 400 described herein may be provided to the user 106 during an exercise class as a means of communicating with, guiding, and/or encouraging the user 106. In some examples, such windows 422 and/or executable controls 418 may not be configured to receive user input and may not be operable to modify on or more parameters of the exercise machine 102. In additional examples, on the other hand, one or more of the executable controls 418 provided at 904 may be configured to receive a touch input from the user 106 via the display 104. In such examples, the one or more of the executable controls 418 may be configured to modify at least one parameter of the exercise machine 102 that the user 106 is utilizing to participate in the exercise class based at least in part on such an input.

At 906, the processor of the digital hardware 148 may receive user data collected while the executable control 418 is displayed via the display 104. Such user data may include, for example, one or more sensor signals, control settings, speed settings, incline settings, resistance settings, cadence settings, and/or other settings of the exercise machine 102 selected by the user 106 during playback of the video file. For example, the processor of the digital hardware 148 may display the executable control 418 during a particular part of the video file received at 902. In such examples, the user data received at 906 may comprise one or more settings (e.g., a first setting) of the exercise machine 102 selected by the user 106 during playback of the particular part of the video file to which the executable control 418 corresponds. In some examples, the first setting of the exercise machine 102 may comprise a current speed of the belt 120, a current incline of the deck 112, a current resistance associated with the belt 120, a current braking resistance, pedal cadence, seat position, and/or other operating parameter of the exercise machine 102, a current power zone of the user 106, and/or any other performance metric. In other examples, the first setting may comprise a setting of the exercise machine 102 selected by the user 106 via one or more controls of the exercise machine 102 separate from the executable control 418 and during display of the executable control 418. In still further examples, the first setting may comprise a setting of the exercise machine 102 that the user 106 selects by providing a touch input via the executable control 418 itself. In such examples, the displayed executable control 418 may be configured to receive a touch input from the user 106, and to modify a parameter of the exercise machine 102 based at least partly on such a touch input.

At 910, the processor of the digital hardware 148 may determine a difference between the first setting included in the user data received at 906, and a second setting associated with the executable control 418 included in the video file received at 902. For example, as noted above executable controls 418 of the present disclosure may include one or more respective settings. In embodiments in which the executable control 418 is generated based on a relatively specific performance command uttered by the instructor, the server 302 may configure the executable control 418 such that, when the executable control 418 is processed and/or executed by the processor of the digital hardware 148, the processor of the digital hardware 148 may cause a component of the exercise machine 102 (e.g., a motor of the deck 112 controlling the speed of the belt 120) to operate and/or perform an action specifically defined by the corresponding setting of the executable control 418. For example, in embodiments in which an instructor utters the relatively specific command "run at a 6.0 minute mile pace," the server 302 may generate a corresponding executable control 418 that includes instructions, metadata, and/or other information or components (e.g., settings) which, when executed by the processor of the digital hardware 148, will cause the motor of the deck 112 controlling the speed of the belt 120 to drive the belt 120 to rotate at a belt speed corresponding to a 6.0 minute mile pace. Similar settings may be included in an executable control 418 directed to a particular power zone, a particular incline of the deck 112, a particular pedal cadence, a particular stationary bicycle braking resistance, and/or any other parameter of the exercise machine 102.

On the other hand, in embodiments in which the instructor utters a relatively vague or abstract command, the server 302 may configure the executable control 418 such that, when the executable control 418 is processed and/or executed by the processor of the digital hardware 148, the processor of the digital hardware 148 may determine an appropriate (e.g., a best fit) response corresponding to the executable control 418 settings before causing one or more components of the exercise machine 102 to operate in a modified manner. For example, in embodiments in which an example relatively abstract instructor command comprises "jog for a few minutes," the server 302 may generate an executable control 418 including settings which when executed by the processor of an exercise machine 102 may cause the belt 120 of such an exercise machine 102 to rotate at a 4.0 minute mile pace, and/or at any other relatively common jogging pace, and such a setting of the executable control 418 may comprise a default setting. Alternatively, in examples in which a user profile of the user 106 identifies a preferred jogging pace, and/or in which the database 304 includes stored user data or other information indicating previously selected, previously customized, and/or previously entered jogging speeds of the particular user 106, a weight, height, age, gender, or other physical characteristics of the user 106, and/or other such information, the server 302 may generate an executable control 418 configured to cause the belt 120 to rotate at a jogging pace that corresponds to such user-specific information.

In any of the examples described herein, at 908 the processor of the digital hardware 148 may determine a difference between a current setting of the exercise machine 102 and one or more settings of the executable control 418. For example, in instances in which, upon viewing the executable control 418 displayed at 904, the user 106 modifies the various settings of the exercise machine 102 to match the settings associated with the executable control 418, the difference, determined at 908 may be approximately zero. In such examples, the user 106 may be operating the exercise machine 102, in accordance with the settings of the executable control 418. For instance, the user 106 may have provided a touch input via the displayed executable control 418, and as a result, the processor of the digital hardware 148 may have modified the settings of the exercise machine 102 to match the settings of the executable control 418. Alternatively, upon viewing the executable control displayed at 904, the user 106 may have provided an input via one or more controls of the exercise machine 102, separate from the executable control 418, to modify the settings of the exercise machine 102 to match the settings of the executable control 418. The processor of the digital hardware 148 may have modified the settings of the exercise machine 102, based at least in part on such input.

In still further examples, on the other hand, the user 106 may wish to approximate the settings of the executable control 418. For instance, the user 106 may wish to exceed the settings indicated by the executable control 418 (e.g., although the executable control 418 includes a "6.0 minute mile pace" setting, the user 106 wishes to run at a 5.0 minute mile pace). Alternatively, the user 106 may wish to exercise at a slightly reduced intensity level (e.g., although the executable control 418 includes a "6.0 minute mile pace" setting, the user 106 wishes to run at a 7.0 minute mile pace). In any of the examples described above, at 908 the processor of the digital hardware 148 may determine a difference between the setting of the exercise machine 102 and the corresponding setting of the executable control 418.

At 910, the processor of the digital hardware 148 may generate an accuracy metric based at least in part on the difference, determined at 908. Such an accuracy metric may comprise, among other things, any number (e.g., a difference, an average, a mode, a median, etc.), parameter, or other indicator of how accurately or inaccurately the user 106 is following the settings of the executable control 418. It is understood that in some examples, such settings of the executable control 418 may correspond to the performance command uttered by the instructor. Such an example accuracy metric (e.g., −3%) is shown in the window 420 illustrated in FIG. 4. Additionally or alternatively, such an accuracy metric may comprise one or more graphics, images, figures, colors, flashing schema, or other visual indicia to provide an indication of how accurately or inaccurately the user 106 is following the settings of the executable control 418. In any of the examples described herein (e.g., in the examples described above with respect to at least FIGS. 4-6), the accuracy metric generated at 910 may be displayed and/or otherwise provided via the display 104.

At 912, the processor of the digital hardware 148 may determine whether the accuracy metric generated at 910 is outside of a desired accuracy range. For example, at 912 the processor of the digital hardware 148 may compare the accuracy metric generated at 910 to a range of values, comprising such an accuracy range. In examples in which the determined accuracy metric (e.g., a determined accuracy value) is either above the upper bounds or below the lower bounds of such an accuracy range (912—Yes), the processor of the digital hardware 148 may cause the display of and/or may otherwise provide a notification to the user 106 via the display 104. Such an example notification may comprise an encouragement, helpful tips, guidance, and/or other information that may be useful to the user 106, in order to achieve the settings corresponding to the displayed executable control 418. As shown in FIG. 4, an example notification or other corresponding information (e.g., "C'mon, let's pick up the pace!") may be provided at 914 via one or more windows 422 of a user interface 400. At 914, and based at least in part on determining that the accuracy metric generated at 910 is outside of the accuracy range, the processor of the digital hardware 148 may provide a notification to the user 106, via a window 422, associated with the setting of the executable control 418.

Alternatively, if the determined accuracy metric (e.g., a determined accuracy value) is less than or equal to the upper bounds of the accuracy range, and is greater than or equal to the lower bounds of such an accuracy range (912—No), at 916 the processor of the digital hardware 148 may provide the accuracy metric to the user 106 via the display 104. For example, as shown in at least FIG. 4, such an accuracy metric may be provided via a window 420 and/or other portion of a user interface 400 configured to provide information to the user 106 during participation in an exercise class. In some examples, if the determined accuracy metric (e.g., a determined accuracy value) is less than or equal to the upper bounds of the accuracy range, and is greater than or equal to the lower bounds of such an accuracy range (912—No), operation 914 may be omitted.

It is understood that in any of the examples described herein, providing the accuracy metric at 916 may include providing the accuracy metric generated at 910 to a processor (e.g., a processor of the server 302) remote from the exercise machine 102 via the content distribution network 306. In such examples, and as illustrated by the example user interface 500 of FIG. 5, the processor of the digital hardware 148 may receive, from the remote processor (e.g., from the processor of the server 302), and based at least in part on providing the accuracy metric to the remote processor, information indicative of a plurality of additional accuracy metrics. In such examples, each metric of the plurality of additional accuracy metrics may be associated with a respective user participating in the exercise class. As described above, via the content distribution network 306, a plurality of additional users 106 may utilize respective exercise machines 102, at disparate locations, to participate in the exercise class substantially simultaneously or at dates/times that are convenient for the respective users 106. In such examples, the processor of the digital hardware 148 may display and/or otherwise provide at least a portion of the received information, via the display 104, while providing the content via the display 104 at 904. For example, as shown in FIG. 5 an example user interface 500 may include, among other things, a leaderboard 502. Such a leaderboard 502 may provide information 504 indicating the ranking of one or more of the users participating (currently or previously) in the present exercise class. Such a ranking may be, for example, a numerical ranking (e.g., 1-6,936 users, as indicated in the example leaderboard 502 of FIG. 5) indicating the position, ranking, or rating of one or more of the users. Such ranking may be based on output, pace, speed, accuracy, or any of the other performance metrics described herein. For instance, the leaderboard 502 may include information 508 indicating the accuracy with which each of the listed users are following the current instruction provided by the instructor.

It is also understood that in any of the examples described herein, providing the accuracy metric at 916 may include displaying a user interface that includes a plot line indicative of the accuracy metric over time. For example, as illustrated in FIG. 6, an example user interface 600 may include, among other things, a workout summary window 606 providing a plurality workout information 608. In such examples, such workout information 608 may include one or more workout summary, graphics 610, 612, 614. As described above, such workout summary graphics 610, 612, 614 may each include a respective plot line 616*a*, 616*b*, 616*b*. Such plot lines 616*a*, 616*b*, 616*b* may be illustrative of performance metrics associated with a particular user 106, and recorded during participation of the user 106, in an exercise class. For example, the plot line 616*a* may be indicative of changes in the output of the user 106 over the duration of a particular exercise class, the plot line 616*b* may be indicative of changes in the speed at which the user 106 jogged or ran over the duration of the exercise class, and the plot line 616*c* may be indicative of changes in the accuracy metric described above over the duration of the exercise class. In such examples, providing the accuracy metric may also include displaying a user interface 600 that includes a timeline, such as the segmented timeline 402 shown in FIG. 6, identifying one or more segments of the exercise class. As noted above with respect to FIG. 6, in such examples, the segmented timeline 402 may be displayed in association with the respective workout summary graphics 610, 612, 614 such that activities/segments of the workout corresponding to respective portions of, for example, the plot lines 616*a*, 616*b*, 616*b* can be easily identified by the user 106 via the user interface 600.

Figure 10:
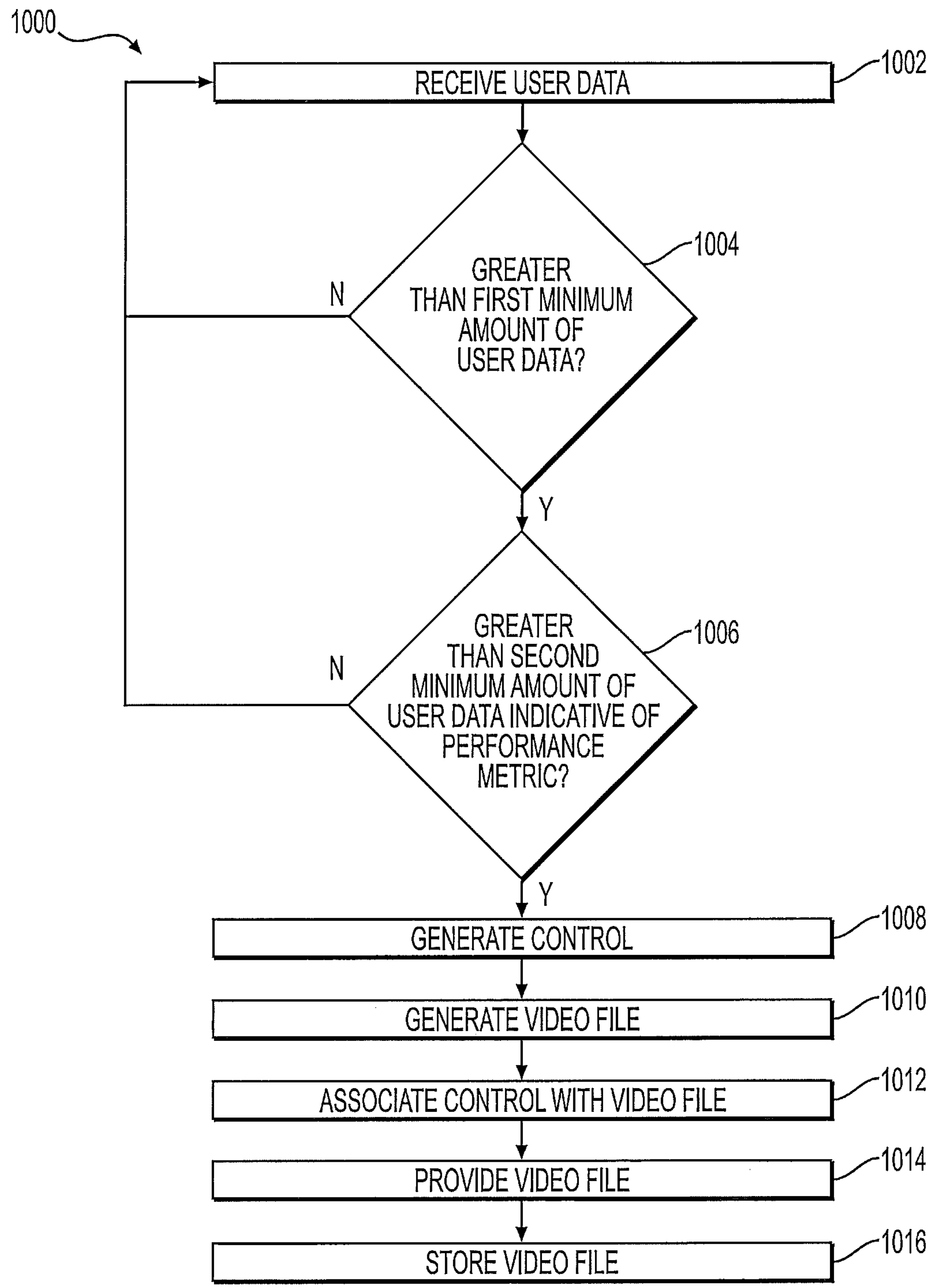
FIG. 10 illustrates a flowchart indicative of still another example method of the present disclosure.

FIG. 10 illustrates a flow chart depicting still another example method 1000 of the present disclosure. Similar to the method 800, the example method 1000 is illustrated as a collection of steps in a logical flow diagram, which represents operations that can be implemented in hardware, software, or a combination thereof. In the context of software, the steps represent computer-executable instructions stored in memory. When such instructions are executed by, for example, the processor of the digital hardware 148 and/or by one or more processors of the server 302 described above, such instructions may cause the processor of the digital hardware 148 and/or the one or more processors of the server 302 to perform the recited operations. Such computer-executable instructions may include routines, programs, objects, components, data structures, and the like that perform particular functions or implement particular abstract data types. The order in which the operations are described is not intended to be construed as a limitation, and any number of the described steps can be combined in any order and/or in parallel to implement the process. For discussion purposes, and unless otherwise specified, the method 1000 is described with reference to the networked exercise system 300, the one or more processors of the server 302, one or more remote exercise machines 102 in communication with the server 302 via the content distribution network 306, the user interfaces 200, 400, 500, 600, 700, and/or other items shown in FIGS. 1-7. In particular, although any part of and/or the entire method 1000 may be performed by the processor of the digital hardware 148, the method 1000 will be described below with respect to the one or more processors of the server 302, and/or other components of the networked exercise system 300, unless otherwise specified, for ease of description.

In example embodiments of the present disclosure, the example method 1000 of FIG. 10 may include, among other things, providing a first video file to a plurality of exercise machines 102. For example, the method 1000 may include providing, with the one or more processors of the server 302, a video file to a plurality of exercise machines 102 via the content distribution network 306. In such examples, the video file may include audio content and video content of an instructor performing an exercise class. Further, it is understood that in some examples the video file may comprise a live stream of the instructor performing the exercise class in substantially real-time. In other examples, on the other hand, the video file may comprise a recording of the instructor performing the exercise class at a previous date/time.

At 1002, the one or more processors of the server 302 may receive user data from the plurality of exercise machines 102. For example, such user data may include respective settings (e.g., exercise machine settings) associated with one or more performance metrics. In some examples, the respective settings included in the user data received at 1002 may be associated with a common performance metric (e.g., an incline of the deck 112, a speed of the belt 120, a resistance of the belt 120, pedal cadence, heart rate, pace, output, etc.). For example, respective settings (e.g., exercise machine settings) included in the user data received at 1002 may be settings utilized by users 106 of the plurality of exercise machines 102 during playback of a particular part of the first video file. For example, at a particular part of the first video file, the instructor may provide a performance command requesting that the users 106 participating in the exercise class run at a 6.0 minute mile pace. Based at least in part on hearing such a performance command, the users 106 participating in the exercise class may modify one or more settings of their respective exercise machines 102 in order to achieve (or attempt to achieve) the pace corresponding to the performance command. Similarly, one or more settings of the respective exercise machines 102 may be modified by the users 106 in order to achieve a resistance, an incline, a heart rate, a pedal cadence, and output, and/or any other performance metric corresponding to a performance command uttered by the instructor during the exercise class. The user data received by the one or more processors of the server 302 at 1002 may include respective settings associated with any such performance metrics.

As described above, example exercise machines 102 of the present disclosure may include one or more sensors 147 configured to sense, collect, measure, and/or otherwise determine performance metrics of the user 106, settings of the exercise machine 102, and/or other information. For example, one or more such sensors 147 may comprise a heart rate monitor, a proximity sensor, and/or other biometric sensor configured to sense, collect, measure, and/or otherwise determine a heart rate, a blood pressure, a body temperature, and/or other physical characteristics of the user 102 as the user participates in an exercise class using the exercise machine 102. The exercise machine 102 may also include one or more additional sensors configured to sense, collect, measure, and/or otherwise determine a speed of the belt 120, an incline of the deck 112, a resistance of the belt 120, a rotational speed of an output shaft of the motor utilized to drive the belt 120, a position of an output shaft of the motor utilized to modify the incline of the deck 112 relative to the support surface on which the exercise machine 102 is disposed, a pedal cadence of a stationary bicycle, a braking force or resistance of the stationary bicycle, and/or other settings of the exercise machine 102. In such examples, the one or more sensors 147 may include, among other things, a proximity sensor, an accelerometer, a gyroscope, and/or other sensors configured to determine speed, motion, position, and/or other parameters or settings. In any of the examples described herein, at 1002 one or more such sensors 147 may provide signals (e.g., continuously, substantially continuously, and/or at regular intervals) to the one or more processors of the server 302, via the content distribution network 306, including such user data.

At 1004, the one or more processors of the server 302 may determine whether the user data received at 1002 comprises greater than a first minimum amount of user data required to generate an executable control 418 of the present disclosure. For example, in order to determine, with a relatively high degree of confidence, one or more settings of an executable control 418 being generated by the one or more processors of the server 302, the one or more processors of the server 302 may determine whether a minimum amount of user data has been received. For instance, in embodiments in which user data associated with only a single user 106 (e.g., a minimum amount equal to two users 106 or two exercise machines 102) has been received at 1002, the one or more processors of the server 302 may determine that the amount of user data received at 1002 is less than the minimum required amount (1004—No). In such embodiments, the one or more processors of the server 302 would proceed to step 1002. On the other hand, in embodiments in which user data associated with three or more users 106 (e.g., a minimum amount equal to two users or two exercise machines 102) has been received at 1002, the one or more processors of the server 302 may determine that greater than a minimum required amount of user data (e.g., first user data associated with a first user 106, combined with second user data associated with a second user 106, and combined with third user data associated with a third user 106) has been received at 1002 (1004—Yes). In such embodiments, the one or more processors of the server 302 would proceed to step 1006.

At 1006, the one or more processors of the server 302 may determine whether the user data received at 1002 is characterized by, is indicative of, and/or otherwise corresponds to one or more metrics above a required threshold. For example, even in embodiments in which greater than a minimum amount of user data has been received at 1002 (1004—Yes), such user data may or may not be sufficient to determine one or more settings of an executable control 418 and/or otherwise sufficient to generate such an executable control 418. For instance, one or more minimum percentage thresholds, minimum length of time thresholds, frequency ranges, minimum and/or maximum parameter values, and/or other metrics may be established and/or otherwise utilized in the process of generating an executable control 418. In any of the examples described herein, at 1006 the one or more processors of the server 302 may compare the user data received at 1002 with one or more such thresholds and/or other metrics in order to determine whether the received user data satisfies such thresholds and/or other metrics.

For example, in one embodiment, one or more such thresholds and/or other metrics may comprise a second minimum percentage (e.g., 50% of all users 106, 60% of all users 106, 70% of all users 106, etc.) or amount (e.g., 100 users, 200 users, 300 users, etc.) of user data that is determined to be indicative of a common performance metric across the plurality of exercise machines 102 used to participate in the exercise class. In such an example embodiment, if greater than a second minimum amount of users 106 (e.g., 50% of all users 106; 100 users, etc.) utilized a common belt speed (e.g., a speed corresponding to a 6.0 minute mile pace) during playback of a particular part of the first video file at which the instructor provided a performance command (1006—Yes), the one or more processors of the server 302 would proceed to step 1008. Alternatively, if less than or equal to such a second minimum amount of users 106 (e.g., 40% of all users 106; 90 users, etc.) utilized a common belt speed (e.g., a speed corresponding to a 6.0 minute mile pace) during playback of a particular part of the first video file at which the instructor provided a performance command (1006—No), the one or more processors of the server 302 would proceed to step 1002.

At 1008, the one or more processors of the server 302 may generate one or more executable controls 148 for a user interface 400, 500 based at least in part on the user data received at 1002. In such examples, the one or more executable controls 148 generated at 1008 may correspond to the common performance metric associated with the respective settings included in the user data received at 1002. Further, in some examples, one or more executable controls 418 generated at 1008 may be operable to modify a parameter of an exercise machine 102 being utilized by a user 106 to participate in the exercise class. In other examples, on the other hand, one or more executable controls 418 generated at 1008 may comprise a message or information provided by the instructor and may not be configured to receive an input from users 106.

As noted above, one or more executable controls 418 may comprise data files, text files, digital files, metadata, instructions, and/or any other electronic file executable by the processor of the digital hardware 148. When an example executable control 418 generated at 1008 is executed by the processor of the digital hardware 148, the processor may cause display of the text or other information associated with the executable control 418 via a user interface (e.g., user interface 400). In some examples, such text (e.g., guidance, an encouraging statement, etc.) may be displayed via one or more respective windows 422 included in the user interface 400. In some examples, such windows 422, executable controls 418, and/or other portions of the example user interfaces 400 described herein may be provided to the user 106 during an exercise class as a means of communicating with, guiding, and/or encouraging the user 106. In some examples, such windows 422 and/or executable controls 418 may not be configured to receive user input and may not be operable to modify on or more parameters of the exercise machine 102. In additional examples, on the other hand, one or more of the executable controls 418 described herein may be configured to receive a touch input from the user 106 via the display 104. In such examples, the one or more of the executable controls 418 may be configured to modify at least one parameter of an exercise machine 102 that a user 106 is utilizing to participate in the exercise class based at least in part on such an input. In example embodiments of the present disclosure, one or more of the executable controls 418 generated at 1008 may comprise one or more settings associated with modifying a parameter of the exercise machine 102.

For example, at 1008 the one or more processors of the server 302 may identify a timestamp associated with the particular part of the video file at which the respective settings associated with the common performance metric described above are used. At 1008, the one or more processors of the server 302 may also generate the executable control 418 corresponding to the performance metric. In particular, at 1008 the one or more processors of the server 302 may configure the executable control 418 such that, when the executable control 418 is processed and/or executed by the processor of the digital hardware 148 (e.g., of an exercise machine 102), the processor of the digital hardware 148 may cause a component of the exercise machine 102 (e.g., a motor of the deck 112 controlling the speed of the belt 120) to operate and/or perform an action specifically defined by the executable control 418. For example, in embodiments in which the respective settings associated with the common performance metric described above correspond to rotating the belt 120 at a 6.0 minute mile pace, at 1008 the one or more processors of the server 302 may generate a corresponding executable control 418 that includes instructions, metadata, and/or other information or components which, when executed by the processor of the digital hardware 148, will cause the motor of the deck 112 controlling the speed of the belt 120 to drive the belt 120 to rotate at a belt speed corresponding to a 6.0 minute mile pace.

At 1010, the one or more processors of the server 302 may generate a video file (e.g., a second video file) comprising the audio content, the video content, and/or any other content of the first video file described above. For example, such a second video file may comprise audio content and video content of the exercise class performed by the instructor.

At 1012, the one or more processors of the server 302 may embed, link, and/or otherwise associate the executable control 418 (generated at 1008) with the second video file (generated at 1010) such that playback of at least part of the second video file by the processor of the digital hardware 148 via the display 104 may result in display of the executable control 418. In particular, at 1012 the one or more processors of the server 302 may link the executable control 418 to the particular part of the second video file corresponding to the timestamp described above (e.g., the particular part of the second video file at which the instructor utters the performance command corresponding to the executable control 418). In such examples, the timestamp may comprise an elapsed time of the second video file generated at 1010. As a result, when providing the exercise class to the user 106 via a user interface 400, 500 (e.g., either in substantially real time via live streaming, and/or upon playback of the exercise class using an archived video file), the processor of the digital hardware 148 may provide the executable control 418 at the point in time during the exercise class in which the instructor uttered the verbal command. In particular, playback of the second video file may cause display of the executable control 148 at a part of the second video file corresponding to the timestamp. Further, it is understood that in some examples, the processes described herein with respect to step 1012 may be performed during step 1010. In such examples, step 1012 may be omitted.

At 1014, the one or more processors of the server 302 may provide the executable control 418, together with the second video file generated at 1010, to one or more exercise machines 102 via the content distribution network 306. In such examples, the video packetizer 326 of the server 302 may provide one or more signals to a plurality of exercise machines 102 via the network 306, and such signals may include, at least part of the second video file and/or the executable control 418 embedded therein. In some examples, such as an example in which a user 106 is live streaming the exercise class in substantially real-time, the server 302 may provide the second video file generated at 1010 and the executable control 418 generated at 1008, via the network 306, as part of a live stream of the exercise class. Alternatively, in examples in which the user 106 is participating in an archived exercise class, at 1014, the server 302 may provide the second video file generated at 1010 and the executable control 418 generated at 1008, via the network 306, as part of a transmission of the archived exercise class.

In any of the examples described herein, user data may be received, at 1002, from a first plurality of exercise machines 102 used by a first plurality of users 106 to participate in the exercise class. In such examples, the first video file described above may be displayed to the first plurality of users 106 via respective displays 104 of the first plurality of exercise machines 102. Accordingly, the user data received at 1002 may be user data corresponding to the first plurality of users 106. Thus, at 1014 the one or more processors of the server 302 may provide the second video file (generated at 1010) to a second plurality of exercise machines 102 separate from the first plurality of exercise machines 102. The second plurality of exercise machines 102 may be used by a second plurality of users 106 to participate in the exercise class associated with the second video file generated at 1010. In such examples, the second video file may be displayed to the second plurality of users 106 via respective displays 104 of the second plurality of exercise machines 102. Accordingly, in embodiments of the method 1000, the one or more processors of the server 302 may receive additional user data corresponding to the second plurality of users 106. The receipt of such additional user data may be similar to the processes described above with respect to step 1002.

Further, at 1016, the server 302 may save and/or otherwise store the executable control 418 generated at 1008 together with the second video file generated at 1010. In such examples, the executable control 418 may be linked to, embedded within, associated with, and/or otherwise stored with the second video file such that, upon playback of the second video file, the executable control 418 may be displayed as part of a user interface 400, 500 presented to the user 106 via the display 104. Further, while the previous disclosure indicates that the one or more processors of the server 302 may perform one or more operations of the method 1000, in any of the examples described herein, any of the operations described above with respect to the method 1000 may be performed, in whole or in part, by the server 302, an operator of the server 302, an operator of a control station at which an exercise class is being performed by an instructor, and/or by any combination thereof In still further embodiments, any of the methods (e.g., the methods 800, 900, 1000) described herein may be utilized to generate a content file that does not include video content. Such a content file may then be used (instead of the video files described herein with respect to the methods 800, 900, 1000) for one or more of the remaining steps in such methods.

For instance, and by way of example, in some embodiments of the method 800 described above with respect to FIG. 8, at 802 the server 302 and/or other components of the networked exercise system 300 may capture content associated with an exercise class being performed by an instructor, and in such examples, one or more video cameras 308, microphones 310, music players 312, audio mixers 314, and/or other components of the networked exercise system 300 may be utilized by and/or in conjunction with the server 302 to sense, record, and/or otherwise capture the exercise class content at 802. For example, at 802 the server 302 may capture at least audio content corresponding to the exercise class being performed by the instructor. In such examples, at 804, the server 302 may generate a content file comprising the audio content captured at 802. For example, audio content may be captured at 802 in an audio track, and the content file generated at 804 may comprise the audio track without a corresponding video track. In such examples, while video content may also be captured at 802, such video content may not be incorporated into the content file at 804.

In such example embodiments, at 806 the server 302 may identifying a performance command included in the audio content, and the performance command may comprise a command uttered by the instructor during the exercise class. At 806, the server 302 may also identify a timestamp associated with the performance command. In such examples, at 808 the server 302 may generate an executable control corresponding to the performance command as described above, and at 810 the server 302 may associated the executable control with the content file generated at 804. In doing so, at 810 the server 302 may generate an augmented or otherwise modified content file comprising the audio content and the executable control. As noted above, such an augmented or otherwise modified content file may not include video content. Additionally, playback of such a content file may cause display of the executable control and/or output of audio corresponding to the executable control at a part of the content file (e.g., at a part of the audio track) corresponding to the timestamp. At 812, the server 302 may provide the content file to an exercise machine, via a network, based at least in part on a request received via the network. Further, at 814 the server 302 may store the content file.

In any of the examples described herein, such a content file (e.g., a content file that does not include video content) may be utilized in place of the various video files described above. For instance, in some embodiments of the example method 900, such a content file may be received at 902, and the content included in the content file may be provided at 904. Similarly, in some embodiments of the example method 1000, such a content file may be generated by the server 302 at 1010 instead of one or more of the video files described above. In such examples, the server 302 may generate an augmented content file at 1012 by, among other things, associating an executable control with the content file. The server 302 may provide the content file at 1014, and may store the content file at 1016.

CONCLUSION

The subject matter described above is provided by way of illustration only and should not be construed as limiting. Furthermore, the claimed subject matter is not limited to implementations that solve any or all disadvantages noted in any part of this disclosure. Various modifications and changes may be made to the subject matter described herein without following the examples and applications illustrated and described, and without departing from the spirit and scope of the present invention, which is set forth in the following claims.

What is claimed is:

1. An exercise machine comprising:

a display;

a processor configured to:

provide a user interface on a display, the user interface comprising pre-workout information associated with an exercise class, the pre-workout information comprising a physical activity associated with the exercise class;

play a video file on the display, the video file comprising content of the exercise class available to be performed by a user with the exercise machine and an executable control, wherein the executable control is associated with a timestamp in the video file and corresponds to a performance command; and provide, on the user interface on the display, an identification of the executable control associated with the exercise class.

2. The exercise machine of claim 1, wherein the processor is further configured to:

execute the executable control;

determine a difference between a setting in the executable control and a current setting of the exercise machine;

generate an accuracy metric associated with the exercise class, wherein the accuracy metric is based on the difference; and provide, on the user interface of the display, the accuracy metric.

3. The exercise machine of claim 1, wherein the user interface comprises the pre-workout information presented in a window superimposed on a library of exercise classes.

4. The exercise machine of claim 1, wherein the user interface comprises the pre-workout information presented as an icon, an image, text, and/or other indicia.

5. The exercise machine of claim 1, wherein the executable control is executable by the processor to modify an operating parameter of the exercise machine in response to an input received from the user via the executable control and/or in response to a playback of the video file by the processor.

6. The exercise machine of claim 5, wherein the operating parameter comprises at least one of:

a speed of a belt associated with a deck of the exercise machine;

a resistance of the belt; and an incline of the deck.

7. The exercise machine of claim 1, wherein the video file comprises an audio content and a video content, wherein the executable control is generated based at least in part on the performance command in the audio content uttered by an instructor of the exercise class.

8. The exercise machine of claim 7, wherein the executable control is generated in response to voice recognition software operating on the audio content.

9. The exercise machine of claim 8, wherein the voice recognition software is natural language processing software on a server remote from the exercise machine.

10. A method comprising:

providing a user interface on a display of an exercise machine, the user interface comprising pre-workout information associated with an exercise class available to be performed by a user with the exercise machine, the pre-workout information comprising a physical activity associated with the exercise class receiving a user selection of the exercise class on the user interface;

playing a video file on the display, the video file comprising content of the exercise class and an executable control, wherein the executable control is associated with a timestamp in the video file and corresponds to a performance command; and displaying, on the user interface of the display, an identification of the executable control associated with the exercise class.

11. The method of claim 10, further comprising:

determining a difference between a setting in the executable control and a current setting of the exercise machine; and generating an accuracy metric associated with the exercise class.

12. The method of claim 10, wherein the user interface comprises the pre-workout information presented in a window superimposed on a library of exercise classes.

13. The method of claim 10, wherein the user interface comprises the pre-workout information presented as an icon, an image, text, and/or other indicia.

14. The method of claim 10, further comprising executing the executable control by a processor of the exercise machine to modify an operating parameter of the exercise machine in response to an input received from the user via the executable control and/or in response to the playing.

15. The method of claim 14, wherein the operating parameter comprises at least one of:

a speed of a belt associated with a deck of the exercise machine;

a resistance of the belt; and an incline of the deck.

16. The method of claim 10, wherein the video file comprises an audio content and a video content, and wherein the executable control is generated based at least in part on the performance command in the audio content uttered by an instructor of the exercise class.

17. The method of claim 16, wherein the generating comprises operating voice recognition software on the audio content.

18. The method of claim 17, wherein the voice recognition software is natural language processing software on a server remote from the exercise machine.

19. A method comprising:

displaying, using a user interface on a display of an exercise machine, the user interface comprising pre-workout information associated with an exercise class available to be performed by a user with the exercise machine, the pre-workout information comprising a physical activity associated with the exercise class;

providing a user selection of the exercise class on the user interface; and displaying, a video file on the display, the video file comprising content of the exercise class and an executable control, wherein the executable control is associated with a timestamp in the video file and corresponds to a performance command; and displaying, using the user interface an identification of the executable control.

20. The method of claim 19, further comprising:

executing the executable control;

generating an accuracy metric associated with the exercise class, wherein the accuracy metric is based on a difference between a setting in the executable control and a setting in the exercise machine; and displaying, on the user interface of the display, the accuracy metric.

* * * * *

UNITED STATES PATENT AND TRADEMARK OFFICE

CERTIFICATE OF CORRECTION

PATENT NO. : 12,214,260 B2
APPLICATION NO. : 17/862139
DATED : February 4, 2025
INVENTOR(S) : Joseph Intonato and Betina Evancha It is certified that error appears in the above-identified patent and that said Letters Patent is hereby corrected as shown below:

In the Specification

In the CROSS-REFERENCE:

Column 1, Lines 6-7 change “U.S. Patent Application Ser. No.” to --U.S. Patent Application No.--.

Column 1, Line 8 change “U.S. Patent Application Ser. No.” to --U.S. Patent Application No.--.

Column 1, Line 10 change “U.S. Patent Application Ser. No.” to --U.S. Patent Application No.--.

Column 1, Lines 11-12 change “U.S. Patent Application Ser. No.” to --U.S. Patent Application No.--.

Column 1, Lines 16-17 change “U.S. Patent Application Ser. No.” to --U.S. Patent Application No.--.

Column 1, Line 20 change “U.S. Patent Application Ser. No.” to --U.S. Patent Application No.--.

Column 1, Lines 21-22 change “U.S. Patent Application Ser. No.” to --U.S. Patent Application No.--.

Column 1, Lines 23-24 change “U.S. Patent Application Ser. No.” to --U.S. Patent Application No.--.

Column 1, Line 28 change “U.S. Patent Application Ser. No.” to --U.S. Patent Application No.--.

Column 1, Line 29 change “U.S. Patent Application Ser. No.” to --U.S. Patent Application No.--.

Column 1, Lines 30-31 change “U.S. Patent Application Ser. No.” to --U.S. Patent Application No.--.

Column 1, Line 32 change “U.S. Patent Application Ser. No.” to --U.S. Patent Application No.--.

Column 1, Lines 37-38 change “U.S. Patent Application Ser. No.” to --U.S. Patent Application No.--.

Signed and Sealed this
Twenty-fifth Day of March, 2025

Coke Morgan Stewart
*Acting Director of the United States Patent and Trademark Office*

Column 1, Line 39 change “U.S. Patent Application Ser. No.” to --U.S. Patent Application No.--.

Column 1, Line 41 change “U.S. Patent Application Ser. No.” to --U.S. Patent Application No.--.